(12) United States Patent
Neogi et al.

(10) Patent No.: US 7,456,292 B2
(45) Date of Patent: Nov. 25, 2008

(54) HYDROXAMIC ACID-CONTAINING AMINO ACID DERIVATIVES

(75) Inventors: Partha Neogi, Fremont, CA (US);
Debendranath Dey, Fremont, CA (US);
Abjiheet Nag, Fremont, CA (US);
Sujata Neogi, Fremont, CA (US);
Bishwajit Nag, Union City, CA (US)

(73) Assignee: Bexel Pharmaceuticals, Inc., Union City, CA (US)

( * ) Notice: Subject to any disclaimer, the term of this patent is extended or adjusted under 35 U.S.C. 154(b) by 505 days.

(21) Appl. No.: 11/174,302

(22) Filed: Jun. 30, 2005

(65) Prior Publication Data

US 2007/0004776 A1  Jan. 4, 2007

(51) Int. Cl.
*C07D 211/70* (2006.01)
*A01N 43/40* (2006.01)

(52) U.S. Cl. ..................... 546/339; 514/315

(58) Field of Classification Search ............ 514/315; 546/339

See application file for complete search history.

(56) References Cited

U.S. PATENT DOCUMENTS

| | | |
|---|---|---|
| 2004/0204464 A1 | 10/2004 | Al-Abed |
| 2005/0054882 A1 | 3/2005 | Marcoux |
| 2005/0113346 A1 | 5/2005 | Levin et al. |

OTHER PUBLICATIONS

International Search Report and Written Opinion Of The International Searching Authority dated Aug. 7, 2007, for related PCT Application No. PCT/US2006/25571.

G. Carroll, et al., "Antagonism of the IL-6 cytokine subfamily—a potential strategy for more effective therapy in rheumatoid arthritis", *Inflamm. Res.*, 47 (1998), pp. 1-7.

John S. Yudkin, et al., "Inflammation, obesity, stress and coronary heart disease: is interleukin-6 the link?", *Atherosclerosis*, 148 (2000), pp. 209-214.

Alvin S. Stern, et al., "Purification to homogeneity and partial characterization of cytotoxic lymphocyte maturation factor from human B-lymphoblastoid cells", *Proc. Natl. Acad. Sci.*, 87 (1990), pp. 6808-6812.

A.M. Malfait, et al., "Blockade of IL-12 during the induction of collagen-induced arthritis (CIA) markedly attenuates the severity of the arthritis", *Clin. Exp. Immunol*, 111 (1998) pp. 337-383.

Ivan J. Fuss, et al., "Disparate CD4+ Lamina Propria (LP) Lymphokine Secretion Profiles in Inflammatory Bowel Disease", *The Journal of Immunology*, 157 (1996), pp. 1261-1270.

Paola Parronchi, et al., "Type 1 T-Helper Cell Predominance and Interleukin-12 Expression in the Gut of Patients with Crohn's Disease", *Am. J. Pathol.*, 150 (1997) pp. 823-832.

Scott. E. Plevy, et al., "A Role for TNF-α and Mucosal T Helper-1 Cytokines in the Pathogenesis of Crohn's Disease", *The Journal of Immunology*, 159 (1997) pp. 6276-6282.

Markus F. Neurath, et al., "Antibodies to Interleukin 12 Abrogate Established Experimental Colitis in Mice", *Journal of Experimental Medicine*, 182 (1995) pp. 1281-1290.

Stephen J. Simpson, et al., "T Cell-mediated Pathology in Two Models of Experimental Colitis Depends Predominantly on the Interleukin 12/Signal Transducer and Activator of Transcription (Stat)-4 Pathway, but Is Not Conditional on Interferon γ Expression by T Cells", *Journal of Experimental Medicine*, 187 (1998) pp. 1225-1234.

Michael J. Walter, et al., "Interleukin 12 p40 Production by Barrier Epithelial Cells during Airway Inflammation", *Journal of Experimental Medicine*, 193 (2001), pp. 339-351.

C. Natarajan, et al., "Peroxisome proliferators-activated receptor-gamma agonists inhibit experimental allergic encephalomyelitis by blocking IL-12 production, IL-12 signaling and Th1 differentiation", *Genes and Immunity*, 3 (2002), pp. 59-70.

Linda L. Johnson, et al., "Matrix Metalloproteinases", *Current Opinion in Chemical Biology*, 2 (1998) pp. 466-471.

C. Graham Knight, et al., A novel coumarin-labelled peptide for sensitive continuous assays of the matrix metalloproteinases, *Federation of European Biochemical Societies*, 296, 3 (1992) pp. 263-266.

Matthew W. Olson, et al., "Kinetic Analysis of the Binding of Human Matrix Metalloproteinases-2 and -9 to Tissue Inhibitor of Metalloproteinase (TIMP)-1 and TIMP-2", *J. Biol. Chem.*, 272, 47 (1997) pp. 29975-29983.

Augustin Amour, et al., "TNF-α converting enzyme (TACE) is inhibited by TIMP-3", *Federation of European Biochemical Societies*, 435 (1998) pp. 39-44.

*Primary Examiner*—D. Margaret Seaman
*Assistant Examiner*—Nizal S Chandrakumar
(74) *Attorney, Agent, or Firm*—Weaver Austin Villeneuv & Sampson LLP

(57) ABSTRACT

Novel hydroxamic acid containing amino acid derivatives are provided that are useful for treatment of inflammation, inflammatory and immunological diseases; lowering blood glucose, serum insulin, free fatty acids, cholesterol and triglyceride levels; and for treatment or prophylaxis of metabolic disorders.

16 Claims, 9 Drawing Sheets

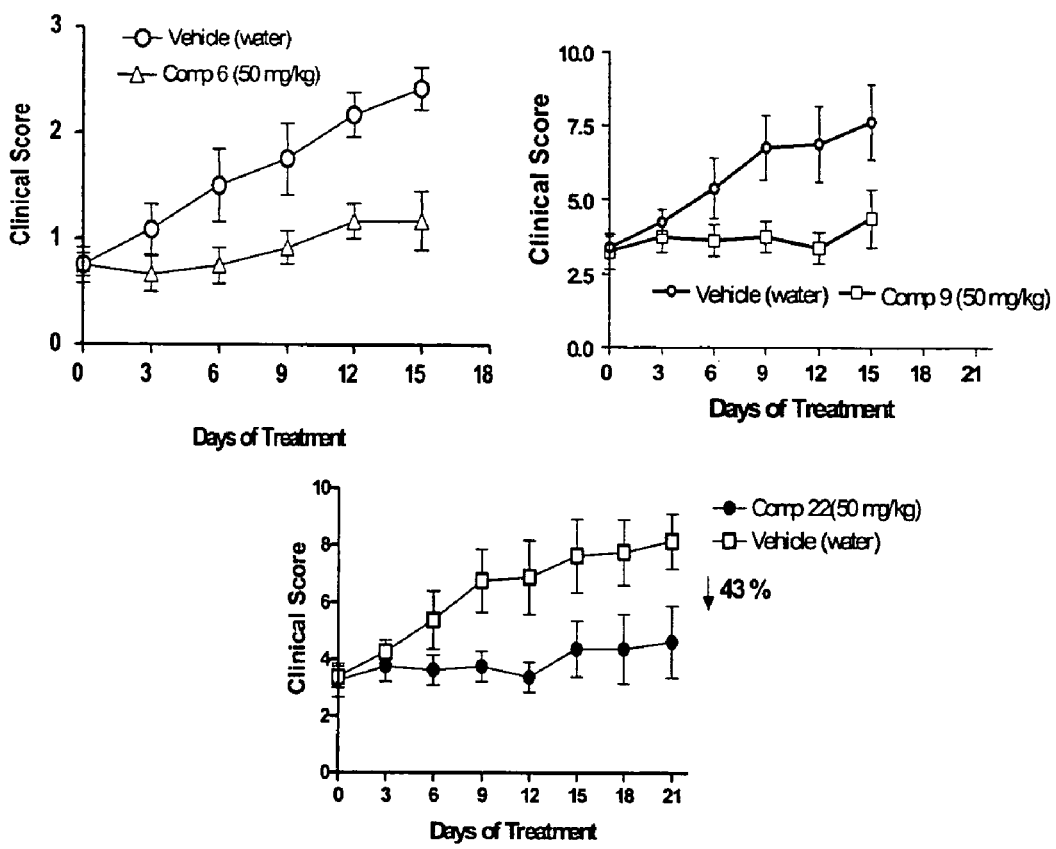

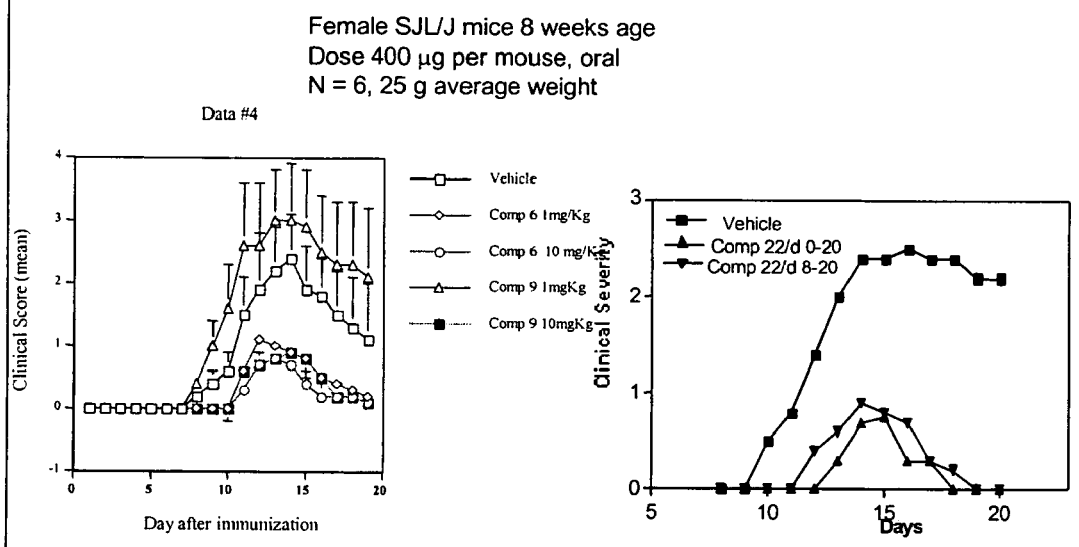

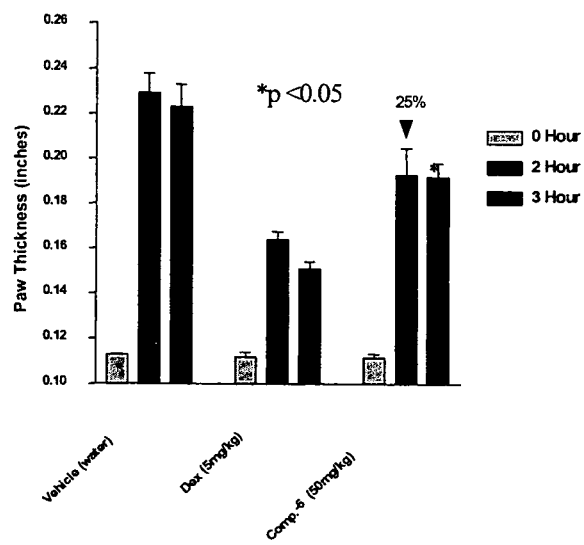
Fig 3. Effect on Carrageenan induced edema

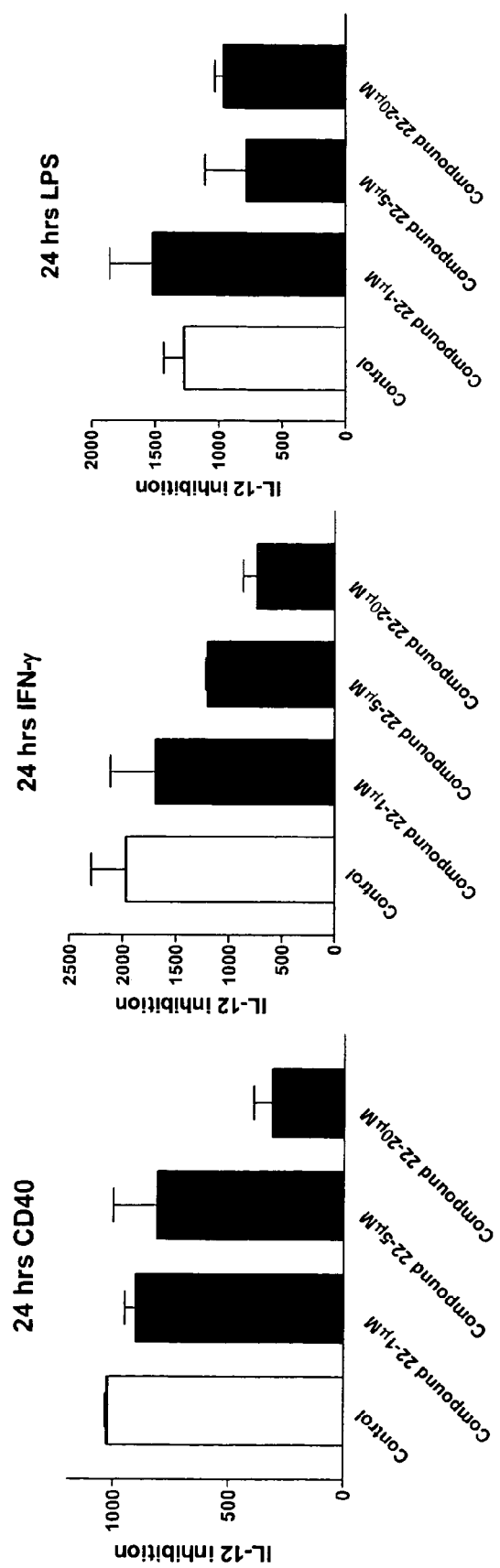
Fig 4. Compound 22 strongly inhibits IL-12 in mouse macrophage

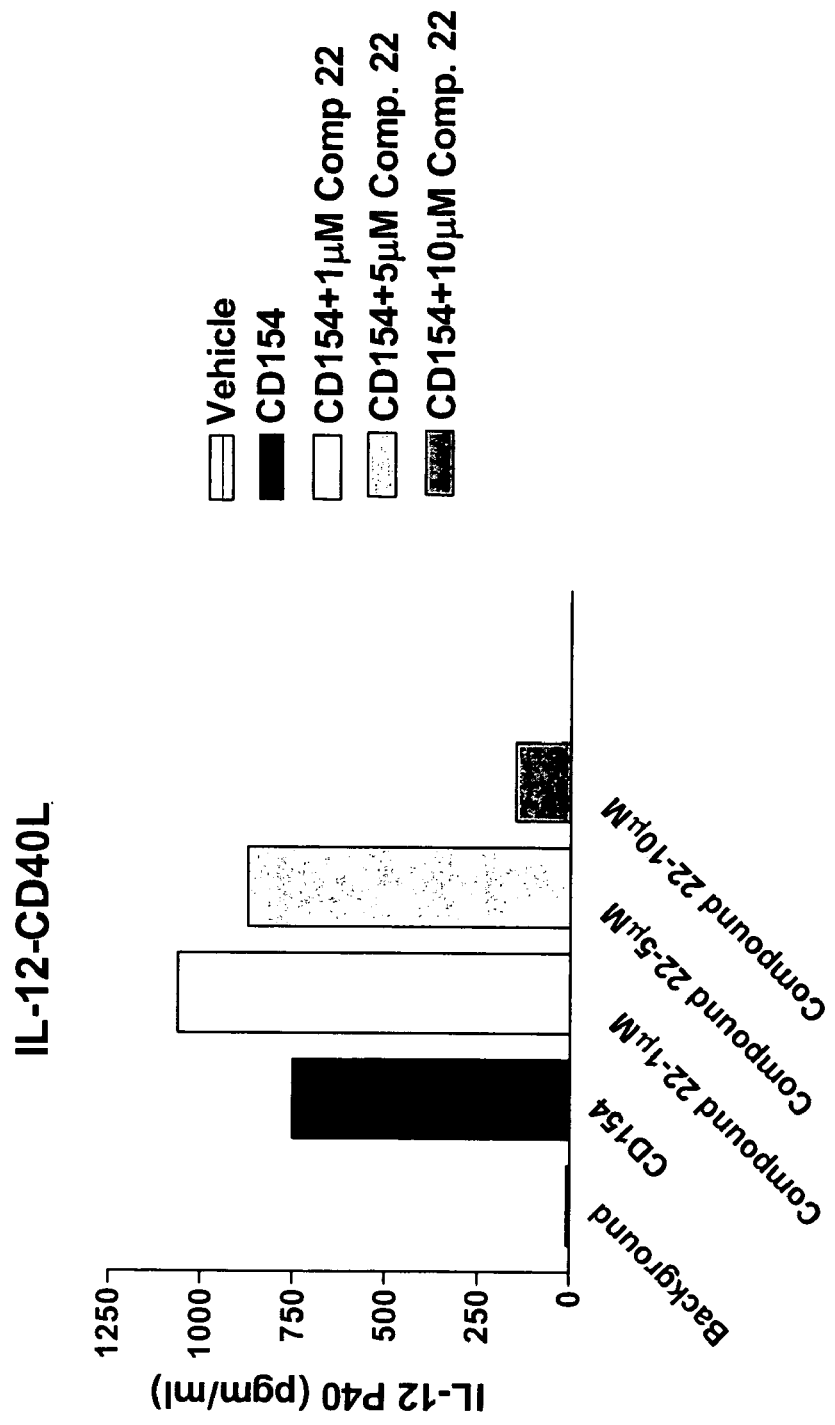
Fig 5. Compound 22 inhibits CD-154 induced IL-12

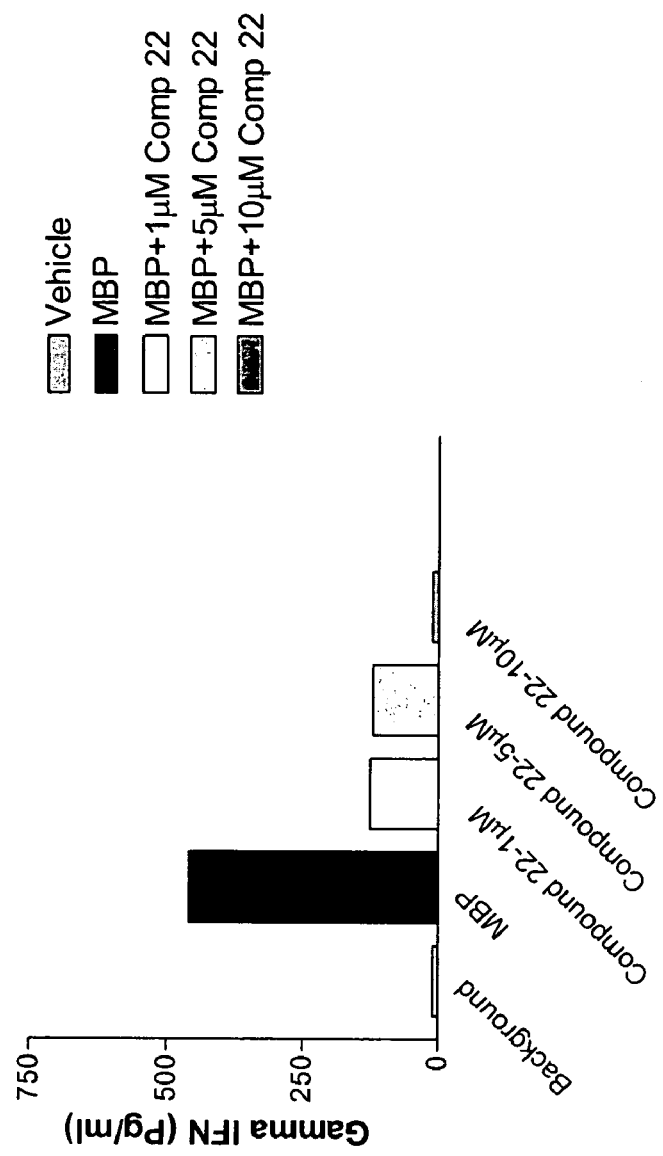
Fig 6. Compound 22 inhibits MBP induced IFN-γ
MBP = Myelin basic protein

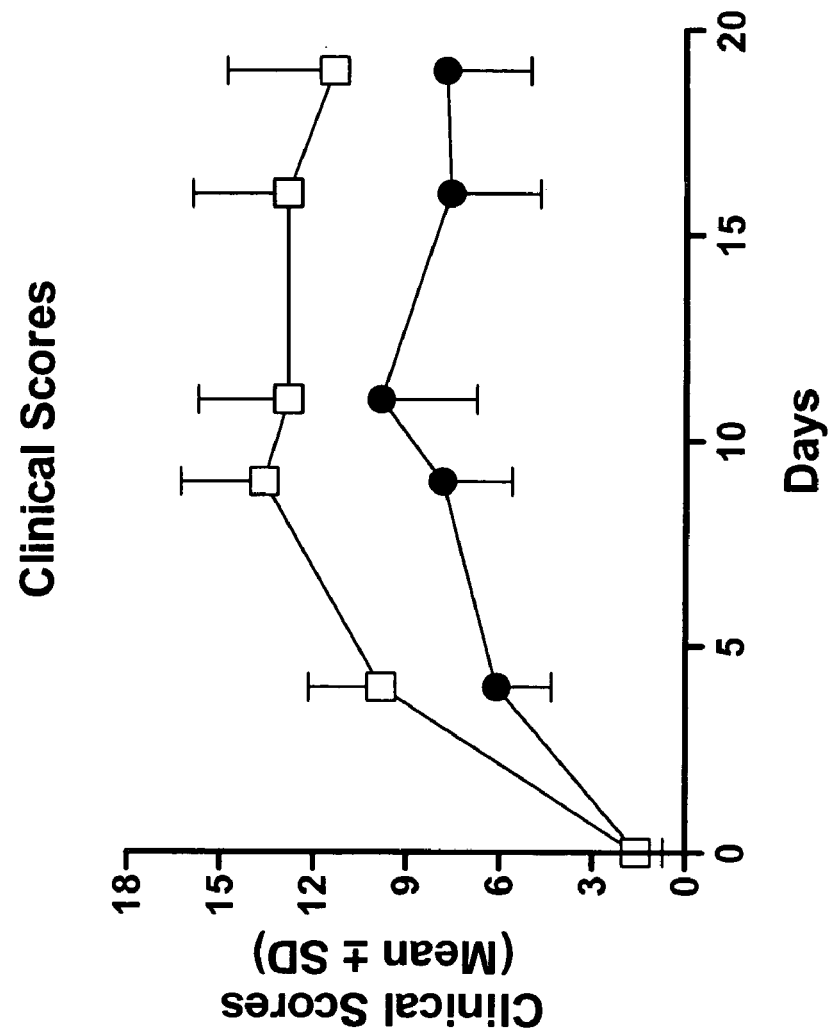
Fig 7. Compound 22 reduces adjuvant induced arthritis (AIA)

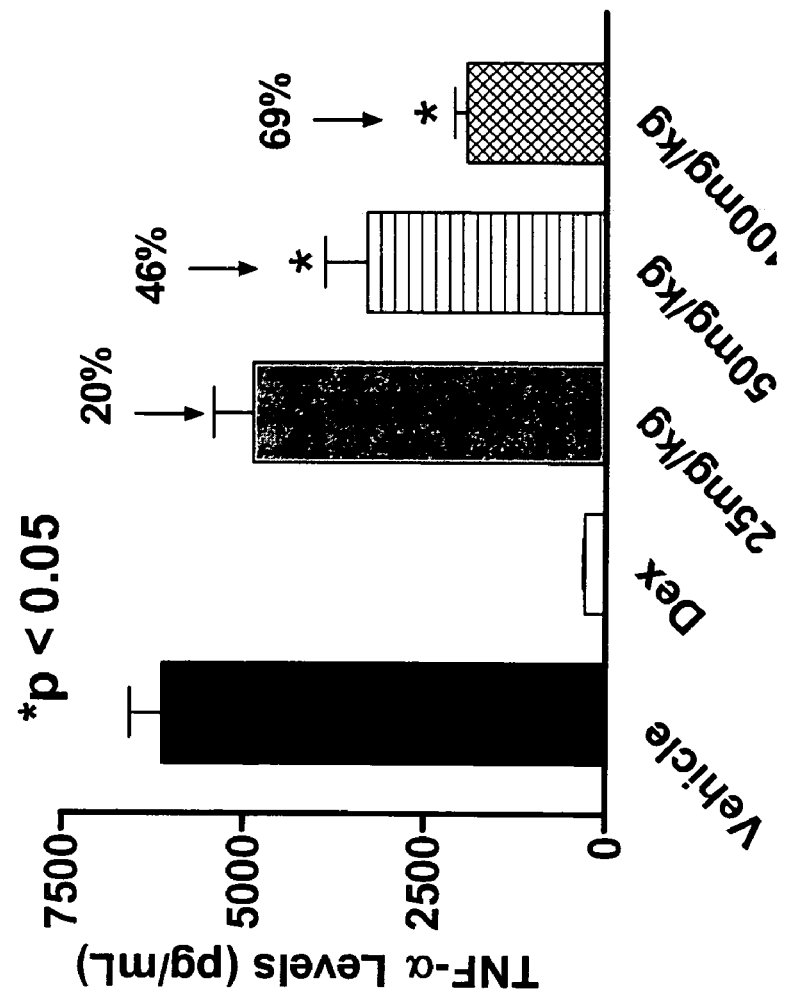
Fig 8. Compound 22 inhibits TNF-α in LPS induced pyresis model

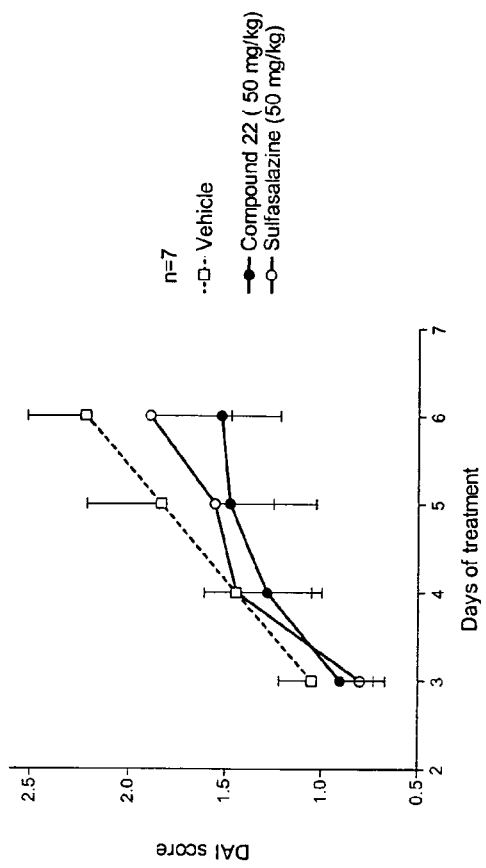
Fig 9. Effect of compound 22 in IBD

HYDROXAMIC ACID-CONTAINING AMINO ACID DERIVATIVES

FIELD OF THE INVENTION

The present invention relates to novel hydroxamic acid-containing amino acid derivatives.

BACKGROUND OF THE INVENTION

The invention provides compositions for the treatment of immunological diseases or inflammation, in particular, such diseases those are mediated by cytokines. The principal elements of the immune system are macrophages or antigen-presenting cells, T cells and B cells. Macrophages are important mediators of inflammation and also provide the necessary "help" for T cell/stimulation and proliferation. For example, macrophages make the cytokines IL-1, IL-6, IL-12 and TNF-α, all of which are potent pro-inflammatory molecules.

TNF-α is a pro-inflammatory cytokine produced by a variety of cell types and expressed on the cell surface as a 233-amino acid 26 kDa membrane-bound precursor protein. TNF-α converting enzyme (TACE) proteolytically cleaves of membrane-bound TNF-α and produces a mature, soluble cytokine of 17 kDa that exists as a non-covalently bound trimmer. The biological effects of TNF-α are intervened by two membrane-bound receptors, designated as p55 and p75. Unregulated production of TNF-α is associated with a number of pathological conditions including diabetes, multiple sclerosis, ulcerative colitis, Crohn's disease, psoriasis, spondylitic arthritis, rheumatoid arthritis, congestive heart failure and may other diseases. Thus the inhibitors of TNF-α are potentially useful in the treatment of a wide variety of diseases.

The cytokine IL-1β also participates in the inflammatory response. It stimulates thymocyte proliferation, fibroblast growth factor activity, and the release of prostaglandin from synovial cells. Elevated or unregulated levels of the cytokine IL-1β have been associated with a number of inflammatory diseases and other disease states, including but not limited to Alzheimer's disease, adult respiratory distress syndrome, allergy, asthma, anorexia, atherosclerosis and pain and inflammation resulting from strain, sprain, trauma, surgery, infection or other disease processes. Since overproduction of IL-1β is associated with numerous disease conditions, it is desirable to develop compounds that inhibit the production or activity of IL-1β.

IL-6 participates in the immune response, hematopoiesis and inflammation. It is a potent inducer of the hepatic acute phase response and is a powerful stimulator of the hypothalamic-pituitary-adrenal axis that is under negative control by glucocorticoids. IL-6 promotes the secretion of growth hormone but inhibits release of thyroid stimulating hormone. Elevated levels of IL-6 are seen in several inflammatory diseases, and inhibition of the IL-6 cytokine subfamily has been suggested as a strategy to improve therapy for rheumatoid arthritis (Carroll et al., Inflamm Res, 47:1-7, 1998). In addition, IL-6 has been implicated in the progression of atherosclerosis and the pathogenesis of coronary heart disease (Yudkin et al., Atherosclerosis, 148:209-14, 1999). Implicated in several disease states, it is highly desirable to develop compounds that inhibit IL-6 secretion.

IL-12 is a heterodimeric cytokine consisting of a p40 and a p35 subunit, with potent immunoregulatory properties, primarily released by antigen-presenting cells, dendritic cells, and monocytes/macrophages in response to bacterial product and immune signals. It enhances natural killer (NK)-mediated cytotoxicity and induces interferon-gamma (IFN-γ) production by NK cells and T lymphocytes. IL-12 plays a key role in promoting Th1 immune responses, demonstrated both in vitro and in vivo. Antibodies against IL-12 have been found to have beneficial effect in experimental models for autoimmune diseases that are Th1-driven, such as experimental allergic encephalomyelitis (EAE) and 2,4,6-trinitrobenzene sulphonic acid (TNBS)-induced chronics intestinal inflammation in mice, a model for human inflammatory bowel disease.

Collagen induced arthritis (CIA) of mouse is an experimental model for rheumatoid arthritis (RA) that can be induced in DBA/1 mice by immunization with heterologous native type II collagen (CII) emulsified in Freund's complete adjuvant (FCA). It has been recently demonstrated that IL-12 can replace *Mycobacterium tuberculosis* when immunizing DBA/1 mice with CII resulting in severe arthritis associated with enhanced IFN-γ production by ex vivo CII-stimulating spleen cells and an increased collagen-specific IgG2a antibody response (Stern, A. S., et al., *Proc. Natl. Acad. Sci*, 1990, 87, 6808). The blockade of IL-12 by administration of anti IL-12 MoAb was not able to prevent the onset of CIA but dramatically reduced the severity of the arthritis (Malfait, A. M., et al., *Clin. Exp. Immunol.*, 1998, 111, 377-383).

Crohn's disease is characterized by increased production of IL-12 by antigen-presenting cells in intestinal tissue and interferon-γ and TNF-α by intestinal lymphocytes and macrophages (Fuss, I. J. et al, *J. Immunol.*, 1996, 157, 1261; Parronchi, P., et al, *Am. J. Pathol.*, 1997, 150, 823; Plevy, S. E. et al, *J. Immunol.*, 1997, 159, 627). These inflammatory cytokines in turn induce and sustain the granulomatous inflammation and bowel-wall thickening that are hallmarks of Crohn's disease. In mice, administration of a monoclonal antibody against IL-12 can result in the resolution of established colitis and, if given at the time of induction of colitis, can prevent inflammation (Neurath, M. F. et al, *J. Exp. Med.*, 1995, 182, 1281). Anti-IL-12 can also prevent and treat the spontaneous colitis seen in models of Th1-mediated inflammation such as mice that over express the human CD3ε gene and mice deficient in interleukin-10 (Simpson, S. J. et al, *J. Exp. Med.*, 1998, 187, 1225).

Similar to IL-12, a related heterodemeric protein IL-23 consists of p19 and p40 subunits. A human antibody directed against p40 thus can effectively block the action of both IL-12 and IL-23. IL-12 and IL-23 are both produced by activated (mature) dendritic cells and are critical in promoting differentiation and proliferation of type 1 cytokine-producing naïve and memory T cells, respectively. The lesions of psoriatic skin shows the excessive presence of: (1) activated dendritic cells; (2) IL-23 and IL-12; and (3) type 1 cytokine-producing CD4+ and CD8+ memory T cells. Thus, the p40 subunit of IL-23/IL-12 is an attractive therapeutic target in psoriasis. Walter and coworkers (*J. Exp. Med.*, 2001, 193, 339) have demonstrated that the cellular source of IL-12 and IL-12 p40 is inducible by viral infection, that there is a new functional consequence of IL-12 p40 production in vivo that is not dependent on actions of IL-12 p70 or IFN-γ, and provided the first proof that epithelial IL-12 p40 expression is abnormally programmed in asthma.

Multiple sclerosis (MS) is an inflammatory demyelinating disease of the central nervous system (CNS) that afflicts around 1 million people worldwide. There is no medical treatment available so far that can cure MS. The pathogenesis of EAE/MS is a complex process that involves activation of macrophage/microglial cells, differentiation of encephalitogenic Th1 cells and secretion of inflammatory cytokines in the CNS. Interleukin-12 is produced mainly by macrophage/microglia that plays a critical role in the differentiation of encephalitogenic Th1 cells and pathogenesis of EAE and MS (Nararajan, C. and Bright, J. J., *Genes and Immunity.*, 2000, 3, 59-70). This shows that IL-12 has a significant role in the pathogenesis of arthritis, multiple sclerosis, asthma, Crohn's disease, inflammatory bowel disease, psoriasis and related autoimmune diseases.

It will be appreciated from the foregoing that, while there have been extensive prior efforts to provide compounds for inhibiting, for example, TNF-α, IL-1β, IL-6 IL-12, or other agents considered responsible for inflammation or inflammatory diseases, e.g. arthritis, there still remains a need for new and improved compounds for effectively treating or inhibiting such diseases.

SUMMARY OF THE DISCLOSURE

The present invention relates to novel amino acids derivatives of the general formula (I)

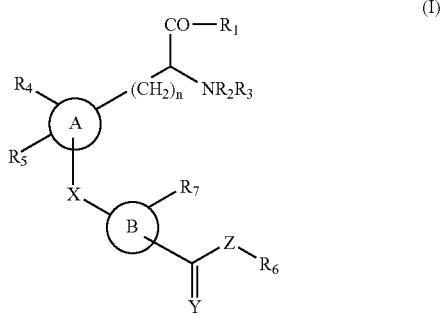

The present invention also relates to a process for the preparation of the above novel compounds, their derivatives, steroisomers, their pharmaceutically acceptable salts and pharmaceutical compositions containing them; wherein A is a 5 to 18-membered aryl or heterocyclyl group, including, but not limited to, substituted or unsubstituted phenyl, indolyl and imidazolyl; B represents a ring system selected from substituted or unsubstituted 5 to 18-membered aryl or 5 to 6 membered saturated or unsaturated heterocyclyl having 1-4 hetero atoms selected from N, O and S; $R_1$ represents —$OR^{10}$ where $R^{10}$ represents hydrogen, substituted or unsubstituted groups selected from alkyl, alkenyl, aryl, aralkyl, heteroaryl, or a counter ion; $NR^{11}R^{12}$, where $R^{11}$ and $R^{12}$ may be same or different and independently represent H, substituted or unsubstituted groups selected from alkyl, alkenyl, aryl or $R^{11}$ and $R^{12}$ together with nitrogen may represent substituted or unsubstituted mono or bicyclic saturated or unsaturated ring system which may contain one or more heteroatoms selected from O, S or N; $R_2$ and $R_3$ may be same or different and independently represent H, $COR^{13}$, substituted or unsubstituted groups selected from alkyl, alkenyl, aryl, heteroaryl, alkylsulfonyl, alkylsulfinyl, arylsulfonyl, arylsulfinyl, alkylthio, arylthio or heterocyclyl; where $R^{13}$ represents H, substituted or unsubstituted groups selected from alkyl, aryl, alkenyloxy, aryloxy, alkoxy or aralkoxy; or the groups $R_2$ and $R_3$ may be joined to together form heterocyclic rings, such as piperidine, morpholine and the like; Z represents O, S or $NR^{14}$, $R^{14}$ represents hydrogen or alkyl; when Z represents O or S, $R_6$ represents hydrogen or substituted or unsubstituted groups selected from alkyl, alkenyl, aryl, aralkyl, cycloalkyl, heteroaryl, heteroaralkyl, heterocyclyl; when Z represents $NR^{14}$, $R_6$ represents H, hydroxy, a protected hydroxyl group, amino, substituted or unsubstituted groups selected from alkyl, haloalkyl, alkenyl, monoalkylamino, dialkylamino, aryl, aralkyl, cycloalkyl, heteroaryl, heteroaralkyl, heterocyclyl; Y represents O, S or $NR^{14}$; n is an integer in the range of 0 to 4; $R_4$, $R_5$, and $R_7$ may be same or different and represent hydrogen, nitro, hydroxy, formyl, azido, halo, or substituted or unsubstituted groups selected from alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid or its derivatives; X represents a bond, O, S, SO or $SO_2$.

The compounds of the present invention are useful for management of disorders such as inflammation, inflammatory and immunological diseases, particularly those mediated by pro-inflammatory cytokines such as tumor necrosis factor-α (TNF-α), interleukine-1β (IL-1β), IL-6 and IL-12. The compounds of the present invention are also useful in lowering blood glucose, serum insulin, free fatty acids, cholesterol and triglyceride levels and are useful in the treatment and/or prophylaxis of metabolic disorders.

BRIEF DESCRIPTION OF THE FIGURES

FIG. 1 is a group of three graphs showing the effect of three compounds of the invention on collagen-induced mice arthritis models.

FIG. 2 is a group of two graphs showing the effect of three compounds of the invention on induced experimental allergic encephalomyelitis in mice.

FIG. 3 is a bar graph showing the lowering of inflammation in carrageenan-induced rats.

FIG. 4 is a group of three graphs showing inhibition of IL-2 in mouse macrophage.

FIG. 5 is a bar graph showing the inhibition by a compound of the invention of CD40 ligand-mediated synthesis of IL-12.

FIG. 6 is a bar graph showing the inhibition by a compound of the invention myelin basic protein-induced IFN-γ.

FIG. 7 is a graph showing reduction by a compound of the invention of adjuvant-induced arthritis in rats.

FIG. 8 is a bar graph showing inhibition by a compound of the invention of TNF-α levels in an LPS-induced pyresis mouse model.

FIG. 9 is a group of two graphs showing the effect of a compound of the invention in inflammatory bowel disease.

DETAILED DESCRIPTION OF THE INVENTION

As used in the present specification, the following words and phrases are generally intended to have the meanings as set forth below, except to the extent that the context in which they are used indicates otherwise.

"Alkyl" is intended to include linear, branched, or cyclic hydrocarbon structures and combinations thereof. Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of $C_{20}$ or below. More preferred alkyl groups are those of $C_{13}$ or below. Still more preferred alkyl groups are those of $C_6$ and below. Cycloalkyl is a subset of alkyl and includes cyclic hydrocarbon groups of from 3 to 13 carbon atoms. Examples of cycloalkyl groups include c-propyl, c-butyl, c-pentyl, norbornyl, adamantyl and the like. In this application, alkyl refers to alkanyl, alkenyl and alkynyl residues; it is intended to include cyclohexylmethyl, vinyl, allyl, isoprenyl and the like.

"Alkylene" is another subset of alkyl, referring to the same residues as alkyl, but having two points of attachment. Examples of alkylene include ethylene (—$CH_2CH_2$—), propylene (—$CH_2CH_2CH_2$—), dimethylpropylene (—$CH_2C(CH_3)_2CH_2$—) and cyclohexylpropylene (—$CH_2CH_2CH(C_6H_{13})$—). When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl.

The term "alkoxy" or "alkoxyl" refers to the group —O-alkyl, preferably including from 1 to 6 carbon atoms of a straight, branched, cyclic configuration and combinations thereof attached to the parent structure through an oxygen. Examples include methoxy, ethoxy, propoxy, isopropoxy, cyclopropyloxy, cyclohexyloxy and the like. Lower-alkoxy refers to groups containing one to four carbons.

The term "amino" refers to the group —$NH_2$. The term "substituted amino" refers to the mono- or di-substituted group —NHR or —NRR where each R is independently selected from the group: optionally substituted alkyl, optionally substituted alkoxy, optionally substituted amino, optionally substituted aryl, optionally substituted heteroaryl, optionally substituted heterocyclyl, acyl, alkoxycarbonyl, sulfanyl, sulfinyl and sulfonyl, e.g., diethylamino, methylsulfonylamino, furanyl-oxy-sulfonamino.

"Aryl" and "heteroaryl" mean a 5 to 18-membered ring. Examples include a 5-, 6- or 7-membered aromatic or heteroaromatic ring containing 0-4 heteroatoms selected from O, N or S; a bicyclic 9- or 10-membered aromatic or heteroaromatic ring system containing 0-4 (or more) heteroatoms selected from O, N or S; or a tricyclic 12- to 14-membered aromatic or heteroaromatic ring system containing 0-4 (or more) heteroatoms selected from O, N or S. The aromatic carbocyclic rings include, e.g., phenyl, naphthalene, indane, tetralin, and fluorene and the aromatic heterocyclic rings include, e.g., imidazole, oxazole, isoxazole, oxadiazole, pyridine, indole, thiophene, benzopyranone, thiazole, furan, benzimidazole, quinoline, isoquinoline, quinoxaline, pyrimidine, pyrazine, tetrazole and pyrazole.

"Halogen" or "halo" refers to fluorine, chlorine, bromine or iodine. Fluorine, chlorine and bromine are preferred. Dihaloaryl, dihaloalkyl, trihaloaryl etc. refer to aryl and alkyl substituted with a plurality of halogens, but not necessarily a plurality of the same halogen; thus 4-chloro-3-fluorophenyl is within the scope of dihaloaryl.

"Heterocycle" means a cycloalkyl residue of 5 to 14 carbon atoms in which one to four of the carbons is replaced by a heteroatom such as oxygen, nitrogen or sulfur. Examples of heterocycles that fall within the scope of the invention include imidazoline, pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), tetrazole, morpholine, thiazole, pyridine, pyridazine, pyrimidine, thiophene, furan, oxazole, oxazoline, isoxazole, oxadiazole, dioxane, tetrahydrofuran and the like.

"Substituted-" alkyl, aryl, heteroaryl and heterocyclyl refer respectively to alkyl, aryl, heteroaryl and heterocyclyl wherein one or more (up to about 5, preferably up to about 3) hydrogen atoms are replaced by a substituent independently selected from the group: optionally substituted alkyl (e.g., fluoroalkyl), optionally substituted alkoxy, alkylenedioxy (e.g. methylenedioxy), optionally substituted amino (e.g., alkylamino and dialkylamino), optionally substituted amidino, optionally substituted aryl (e.g., phenyl), optionally substituted aralkyl (e.g., benzyl), optionally substituted aryloxy (e.g., phenoxy), optionally substituted aralkoxy (e.g., benzyloxy), carboxy (—COOH), carbalkoxy (i.e., acyloxy or —OOCR), carboxyalkyl (i.e., esters or —COOR), carboxamido, aminocarbonyl, benzyloxycarbonylamino (CBZ-amino), cyano, carbonyl, halogen, hydroxy, optionally substituted heteroaryl, optionally substituted heteroaralkyl, optionally substituted heteroaryloxy, optionally substituted heteroaralkoxy, nitro, sulfanyl, sulfinyl, sulfonyl, and thio.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined below. It will be understood by those skilled in the art with respect to any group containing one or more substituents that such groups are not intended to introduce any substitution or substitution patterns that are sterically impractical, synthetically non-feasible and/or inherently unstable.

"Isomers" are different compounds that have the same molecular formula. "Stereoisomers" are isomers that differ only in the way the atoms are arranged in space. "Enantiomers" are a pair of stereoisomers that are non-superimposable mirror images of each other. A 1:1 mixture of a pair of enantiomers is a "racemic" mixture. The term "(.±.)" is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. When the compounds described herein contain olefinic double bonds or other centers of geometric asymmetry, and unless specified otherwise, it is intended that the compounds include both E and Z geometric isomers. Likewise, all tautomeric forms are also intended to be included.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

The term "therapeutically effective amount" or "effective amount" refers to that amount of a compound that is sufficient to effect treatment, as defined below, when administered to a mammal including humans, in need of such treatment. The therapeutically effective amount will vary depending upon the subject and disease condition being treated, the weight and age of the subject, the severity of the disease condition, the particular compound chosen, the dosing regimen to be followed, timing of administration, the manner of administration and the like, all of which can readily be determined by one of ordinary skill in the art.

The term "treatment" or "treating" means any treatment of a disease in a mammal, including:

a) preventing the disease, that is, causing the clinical symptoms of the disease not to develop;
b) inhibiting the disease, that is, slowing or arresting the development of clinical symptoms; and/or
c) relieving the disease, that is, causing the regression of clinical symptoms.

The term "analogs" refers to a set of compounds which differ from one another only by replacement of one or more heteroatoms, such as O, S, or N, with a different heteroatom.

The term "tautomer forms" refers to structural isomers in rapid equilibrium, such as keto and enol forms of acetylacetone. Tautomer forms are capable of reacting according to either form.

The term "polymorphs" refers to the forms of a polymorphic compound. A polymorphic compound is that which can exist in two or more forms, such as two or more crystalline forms.

The term "derivative" refers to a compound obtained from another compound by a simple chemical process; e.g., acetic acid is a derivative of ethanol by oxidation; N-acetyl ethylamine is a derivative of ethylamine by acetylation.

In formula (I), suitable groups represented by A include substituted or unsubstituted phenyl, pyridinyl, indolyl, diazinyl or imidazolyl groups.

Suitable groups represented by B are selected from 5 to 18-membered aryl such as phenyl, naphthyl and the like, which may be further substituted by a substituted or unsubstituted 5 to 6 membered saturated or unsaturated heterocyclic ring is selected from pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, and the like. Particularly suitable compounds include those in which B is substituted or unsubstituted phenyl, pyridinyl or thiazolyl.

Suitable groups represented by $R_1$ include amino, dialkylamino, isopropoxyl, hydroxyl, benzyloxyl, N-acetyl-perhydro-1,4-dithiaindinyl and perhydro-1,4-oxaza-indinyl.

Suitable groups represented by $R_2$ and $R_3$ are selected from H, $COR^{13}$, substituted or unsubstituted linear or branched $C_1$-$C_{20}$ alkyl group such as methyl, ethyl, n-propyl, isopropyl, n-butyl, isobutyl, t-butyl, n-pentyl, isopentyl, hexyl and the like; substituted or unsubstituted linear or branched $C_2$-$C_{20}$ alkenyl such as ethenyl, propenyl, butenyl and the like; aryl such as phenyl, naphthyl and the like, the aryl group may be substituted; alkylsulfonyl group such as methylsulfonyl, ethylsulfonyl, n-propylsulfonyl, iso-propylsulfonyl and the like, the alkylsulfonyl group may be substituted; arylsulfonyl group such as phenylsulfonyl, tolylsulfonyl, or naphthylsulfonyl, the arylsulfonyl group may be substituted; alkylsulfinyl group such as methylsulfinyl, ethylsulfinyl, n-propylsulfinyl, iso-propylsulfinyl and the like, the alkylsulfinyl group may be substituted; arylsulfinyl group such as phenylsulfinyl or naphthylsulfinyl, the arylsulfinyl group may be substituted; alkylthio group such as methylthio, ethylthio, n-propylthio, iso-propylthio and the like, the alkylthio group may be substituted; arylthio group such as phenylthio, or naphthylthio, the arylthio group may be substituted; heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, quinolinyl, dihydroquinolinyl, tetrahydroquinolinyl, isoquinolinyl, dihydroisoquinolinyl, tetrahydroisoquinolinyl and the like, which may be substituted; heterocyclyl group such as pyrrolidinyl, morpholinyl, thiomorpholinyl, piperidinyl, piperazinyl, and the like, which may be substituted. The groups $R_2$ and $R_3$ may be joined to together form heterocyclic rings. Compounds in which $R_2$ and $R_3$ are independently hydrogen or p-toluenesulfonyl are particularly suitable.

Suitable groups represented by $R_6$ are selected from H, hydroxy, protected hydroxy groups which may be ethers, esters substituted benzyl ethyl ethers and the like; amino, substituted or unsubstituted linear or branched $C_1$-$C_{20}$ alkyl group such as methyl, ethyl, n-propyl, isopropyl, n-butyl, isobutyl, t-butyl, n-pentyl, isopentyl, hexyl and the like; substituted or unsubstituted linear or branched $C_2$-$C_{20}$ alkenyl such as ethenyl, propenyl, butenyl and the like; haloalkyl such as chloromethyl, chloroethyl, trifluoromethyl, trifluoroethyl, dichloromethyl, dichloroethyl, trichloromethyl, difluoromethyl, and the like, which may be substituted; monoalkylamino group such as $-NHCH_3$, $-NHC_2H_5$, $-NHC_3H_7$, $-NHC_6H_{13}$, and the like, which may be substituted; dialkylamino group such as $-N(CH_3)_2$, $-NCH_3(C_2H_5)$, $-N(C_2H_5)_2$ and the like, which may be substituted; aryl such as phenyl, naphthyl and the like, the aryl group may be substituted; aralkyl group such as benzyl, phenyl ethyl, phenyl propyl and the like, which may be substituted; cyclo ($C_3$-$C_6$) alkyl group such as cyclopropyl, cyclobutyl, cyclopentyl, cyclohexyl and the like, the cycloalkyl group may be substituted; heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, quinolinyl, dihydroquinolinyl, tetrahydroquinolinyl, isoquinolinyl, dihydroisoquinolinyl, tetrahydroisoquinolinyl and the like, which may be substituted; heterocyclyl group such as pyrrolidinyl, morpholinyl, thiomorpholinyl, piperidinyl, piperazinyl, and the like, which may be substituted; heteroaralkyl, wherein the heteroaryl group is as defined above. Compounds in which $R_6$ are hydroxyl, hydrogen or dialkylamino are particularly suitable.

Suitable groups represented by $R_4$, $R_5$, and $R_7$ are selected from hydrogen, nitro, hydroxy, formyl, azido, halogen atom such as fluorine, chlorine, bromine or iodine; substituted or unsubstituted liner or branched $C_1$-$C_{20}$ alkyl group such as methyl, ethyl, n-propyl, isopropyl, n-butyl, isobutyl, t-butyl, n-pentyl, isopentyl, hexyl and the like; alkoxy group, such as methoxy, ethoxy, n-propoxy, isopropoxy and the like, which may be substituted; acyl group such as $C(=O)CH_3$, $-C(=O)C_2H_5$, $-C(=O)C_3H_7$, $-C(=O)C_6H_{13}$, $-C(=S)CH_3$, $-C(=S)C_2H_5$, $C(=S)C_3H_7$, $-C(=S)C_6H_{13}$ and the like, which may be substituted; cyclo ($C_3$-$C_6$) alkyl group such as cyclopropyl, cyclobutyl, cyclopentyl, cyclohexyl and the like, the cycloalkyl group may be substituted; haloalkyl such as chloromethyl, chloroethyl, trifluoromethyl, trifluoroethyl, dichloromethyl, dichloroethyl, trichloromethyl, difluoromethyl, and the like, which may be substituted; amino, which may be substituted; hydrazine, monoalkylamino group such as $NHCH_3$, $-NHC_2H_5$, $-NHC_3H_7$, $-NHC_6H_{13}$, and the like, which may be substituted; dialkylamino group such as $-N(CH_3)_2$, $-NCH_3(C_2H_5)$, $-N(C_2H_5)_2$ and the like, which may be substituted; acylamino group such as $-NHC(=O)CH_3$, $-NHC(=O)C_2H_5$, $-NHC(=O)C_3H_7$, $-NHC(=O)C_6H_{13}$, and the like, which may be substituted; alkylsulfonyl group such as methylsulfonyl, ethylsulfonyl, n-propylsulfonyl, iso-propylsulfonyl and the like, the alkylsulfonyl group may be substituted; arylsulfonyl group such as phenylsulfonyl or naphthylsulfonyl, the arylsulfonyl group may be substituted; alkylsulfinyl group such as methylsulfinyl, ethylsulfinyl, n-propylsulfinyl, iso-propylsulfinyl and the like, the alkylsulfinyl group may be substituted; arylsulfinyl group such as phenylsulfinyl or naphthylsulfinyl, the arylsulfinyl group may be substituted; alkylthio group such as methylthio, ethylthio, n-propylthio, iso-propylthio and the like, the alkylthio group may be substituted; arylthio group such as phenylthio, or naphthylthio, the arylthio group may be substituted; alkoxycarbonyl group such as methoxycarbonyl, ethoxycarbonyl, n-propoxycarbonyl, isopropoxycarbonyl and the like, the alkoxycarbonyl group may be substituted; aryloxycarbonyl group such as phenoxycarbonyl, napthoxycarbonyl, the aryloxycarbonyl group may be substituted; alkoxyalkyl group such as methoxymethyl, ethoxymethyl, methoxyethyl, ethoxyethyl and the like, which may be substituted; sulfamoyl, carboxylic acid or its derivatives. Compounds in which $R_4$, $R_5$ and $R_7$ are hydrogen are particularly suitable.

Suitable groups represented by $R_{10}$ are selected from hydrogen, substituted or unsubstituted linear or branched $C_1$-$C_{20}$ alkyl group such as methyl, ethyl, n-propyl, isopropyl, n-butyl, isobutyl, t-butyl, n-pentyl, isopentyl, hexyl and the like; substituted or unsubstituted linear or branched $C_2$-$C_{20}$ alkenyl such as ethenyl, propenyl, butenyl and the like; aryl such as phenyl, naphthyl and the like, the aryl group may be substituted; aralkyl group such as benzyl, phenyl ethyl, phenyl propyl and the like, which may be substituted; heteroaryl group such as pyridyl, thienyl, furyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, benzopyranyl, benzofuranyl, benzimidazolyl, benzoxazolyl, benzothiazolyl, benzopyrrolyl, benzoxadiazolyl, benzothiadiazolyl, benzodioxolyl, quinolinyl, dihydroquinolinyl, tetrahydroquinolinyl, isoquinolinyl, dihydroisoquinolinyl, tetrahydroisoquinolinyl and the like, which may be substituted; a counter ion selected from alkali metal such as Li, Na, and K; alkaline earth metal such as Ca and Mg; salts of bases such as ammonium or substituted ammonium salts, diethanolamine, α-phenylethylamine, benzylamine, piperidine, morpholine, pyridine, hydroxyethylpyrrolidine, hydroxyethylpiperidine, choline, tromethamine and the like.

Suitable groups represented by $R^{11}$ and $R^{12}$ are selected from hydrogen, substituted or unsubstituted linear or branched $C_1$-$C_{20}$ alkyl group such as methyl, ethyl, n-propyl, isopropyl, n-butyl, isobutyl, t-butyl, n-pentyl, isopentyl, hexyl and the like; substituted or unsubstituted linear or branched $C_2$-$C_{20}$ alkenyl such as ethenyl, propenyl, butenyl and the like; aryl such as phenyl, naphthyl and the like, the aryl group may be substituted; or $R^{11}$ and $R^{12}$ together with nitrogen may represent substituted or unsubstituted mono or bicyclic saturated or unsaturated ring system selected from pyridyl, pyrrolyl, oxazolyl, thiazolyl, imidazolyl, isooxazolyl, oxadiazolyl, triazolyl, thiadiazolyl, tetrazolyl, pyrimidinyl, pyrazinyl, pyridazinyl, benzimidazolyl, benzoxazolyl, benzothiazolyl, benzopyrrolyl, benzoxadiazolyl, benzothiadiazolyl, benzodioxolyl, quinolinyl, dihydroquinolinyl, tetrahydroquinolinyl, isoquinolinyl, dihydroisoquinolinyl, tetrahydroisoquinolinyl, pyrrolidinyl, morpholinyl, thiomorpholinyl, piperidinyl, piperazinyl and the like, which may be substituted. The substituents are selected from nitro, hydroxy, halo, formyl, azido, alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acid or its derivatives where $R^{13}$ represents H, substituted or unsubstituted alkyl, aryl, alkenyloxy, aryloxy, alkoxy or aralkoxy group; such as, linear or branched $C_1$-$C_{20}$ alkyl, such as methyl, ethyl, n-propyl, isopropyl, n-butyl, isobutyl, t-butyl, n-pentyl, isopentyl, hexyl and the like; substituted or unsubstituted linear or branched $C_2$-$C_{20}$ alkenyloxy such as ethenyoxyl, propenyloxy, butenyloxy and the like; aryl such as phenyl, naphthyl and the like; linear or branched $C_2$-$C_{20}$ alkoxy such as n-butoxy, isobutoxy, t-butoxy and the like; aryloxy such as phenoxy and the like; aralkoxy such benzoxy and the like.

Suitable groups represented by $R^{14}$ are selected from H, substituted or unsubstituted linear or branched $C_1$-$C_{20}$ alkyl group such as methyl, ethyl, n-propyl, isopropyl, n-butyl, isobutyl, t-butyl, n-pentyl, isopentyl, hexyl and the like.

Suitable groups represented by X are selected from a bond, O, S, SO, $SO_2$. Compounds in which X is a bond or O are particularly suitable.

Suitable groups represented by Y are selected from O, S or $NR^{14}$. Compounds in which Y is O are particularly suitable.

Suitable n is an integer of 0 to 4. Compounds in which n is 0, 1 or 2 are particularly suitable.

Suitable groups represented by Z are selected from O, S or $NR^{14}$. Compounds in which Z is NH or O are particularly suitable.

Suitable substituents on the groups represented by $R_1$, $R_2$, $R_3$, $R_4$, $R_5$, $R_6$, $R_7$, $R^{10}$, $R^{11}$, $R^{12}$, $R^{13}$, $R^{14}$ are selected from nitro, hydroxy, halo, formyl, azido, alkyl, alkoxy, acyl, cycloalkyl, haloalkyl, amino, hydrazine, monoalkylamino, dialkylamino, acylamino, alkylsufonyl, alkylsulfinyl, arylsulfonyl, arylsulfinyl, alkylthio, arylthio, alkoxycarbonyl, aryloxycarbonyl, alkoxyalkyl, sulfamoyl, carboxylic acids and their derivatives.

Pharmaceutically acceptable salts of the present invention include salts with counter ions of an alkali metal such as Li, Na, and K, an alkaline earth metal such as Ca and Mg, salts of organic bases such as diethanolamine, α-phenylethylamine, benzylamine, piperidine, morpholine, pyridine, hydroxyethylpyrrolidine, hydroxyethylpiperidine, choline and the like, ammonium or substituted ammonium salts and aluminum salts. Salts also include those with counter ion amino acids such as glycine, alanine, cystine, cysteine, lysine, arginine, phenylalanine, guanidine etc. Salts may include acid addition salts where appropriate, such as sulphates, nitrates, phosphates, perchlorates, borates, hydrohalides, acetates, tartrates, maleates, citrates, succinates, palmoates, methanesulphonates, tosylates, benzoates, salicylates, hydroxynaphthoates, benzenesulfonates, ascorbates, glycerophosphates, ketoglutarates and the like. Pharmaceutically acceptable solvates may be hydrates or comprise other solvents of crystallization such as alcohols.

The following compounds are representative of the preferred compounds according to Formula (I):

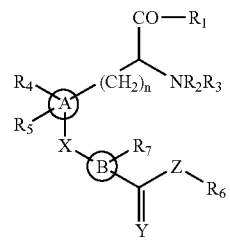

(I)

| $R^1$ | $R^2$ | $R^3$ | $R^6$ | $R^4$ | $R^5$ | $R^7$ | X | Y | Z | n | A | B |
|---|---|---|---|---|---|---|---|---|---|---|---|---|
| —N(CH$_3$)$_2$ | H | H | OH | H | H | H | Bond | O | NH | 1 | Ph | Ph |
| —NH$_2$— | H | H | OH | H | H | H | Bond | O | NH | 1 | Ph | Ph |

-continued

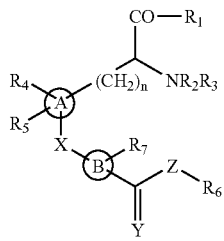

(I)

| R¹ | R² | R³ | R⁶ | R⁴ | R⁵ | R⁷ | X | Y | Z | n | A | B |
|---|---|---|---|---|---|---|---|---|---|---|---|---|
| —NH₂— | H | H | OH | H | H | H | O | O | NH | 1 | Ph | Ph |
| —N(CH₃)₂ | H | H | OH | H | H | H | O | O | NH | 1 | Ph | Ph |
| —N(CH₃)₂ | H | H | OH | H | H | H | Bond | O | NH | 1 | Ph | Py |
| —NH₂— | H | H | OH | H | H | H | Bond | O | NH | 1 | Ph | Py |
| —NH₂— | H | H | OH | H | H | H | O | O | NH | 1 | Py | Ph |
| —N(CH₃)₂ | H | H | OH | H | H | H | O | O | NH | 1 | Py | Ph |
| —N(CH₃)₂ | H | H | OH | H | H | H | Bond | O | NH | 1 | Ph | 2-thienyl |
| —NH₂— | H | H | OH | H | H | H | Bond | O | NH | 2 | Ph | Ph |
| —NH₂— | H | H | OH | H | H | H | O | O | NH | 2 | Ph | Ph |
| —N(CH₃)₂ | H | H | OH | H | H | H | O | O | NH | 2 | Ph | Ph |
| —N(CH₃)₂ | H | H | OH | H | H | H | Bond | O | NH | 2 | Py | Ph |
| —NH₂— | H | H | OH | H | H | H | Bond | O | NH | 2 | Py | Ph |
| —NH₂— | H | H | OH | H | H | H | O | O | NH | 2 | Py | Ph |
| —N(CH₃)₂ | H | H | OH | H | H | H | O | O | NH | 2 | Py | Ph |
| —N(CH₃)₂ | H | H | OH | H | H | H | Bond | O | NH | 1 | Ph | 2-thienyl |
| —NH₂— | H | H | OH | H | H | H | Bond | O | NH | 1 | Ph | Ph |
| —NH₂— | H | H | OH | H | H | H | O | O | NH | 1 | Ph | Ph |
| —N(CH₃)₂ | H | H | OH | H | H | H | O | O | NH | 1 | Ph | Ph |
| —N(CH₃)₂ | H | H | OH | H | H | H | Bond | O | NH | 1 | Py | Ph |
| —NH₂— | H | H | OH | H | H | H | Bond | O | NH | 1 | Py | Ph |
| —NH₂— | H | H | OH | H | H | H | O | O | NH | 1 | Py | Ph |
| —N(CH₃)₂ | H | H | OH | H | H | H | O | O | NH | 1 | Py | Ph |
| —N(CH₃)₂ | H | H | CH₃ | H | H | H | Bond | O | NH | 1 | Ph | Ph |
| —NH₂— | H | H | CH₃ | H | H | H | Bond | O | NH | 1 | Ph | Ph |
| —N(CH₃)₂ | H | —SO₂-C₆H₄-CH₃ | OH | H | H | H | Bond | O | NH | 1 | Ph | Ph |
| —N(CH₃)₂ | H | —SO₂-C₆H₄-CH₃ | H | H | H | H | Bond | O | O | 1 | Ph | Ph |
| —N(CH₃)₂ | H | H | H | H | H | H | Bond | O | O | 1 | Ph | Ph |
| —N(CH₃)₂ | H | H | —N(CH₃)₂ | H | H | H | O | O | NH | 0 | Ph | Ph |
| —N(CH₃)₂ | H | H | H | H | H | H | O | O | NH | 0 | Ph | Ph |
| —N(CH₃)₂ | H | H | H | H | H | H | O | O | O | 0 | Ph | Ph |
| —N(CH₃)₂ | H | H | OH | H | H | H | O | O | NH | 0 | Ph | Ph |

-continued

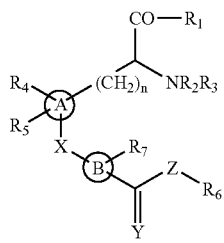

(I)

| R¹ | R² | R³ | R⁶ | R⁴ | R⁵ | R⁷ | X | Y | Z | n | A | B |
|---|---|---|---|---|---|---|---|---|---|---|---|---|
| ![iPrO] | H | H | H | H | H | H | O | O | O | 1 | Ph | Ph |
| ![iPrO] | H | H | OH | H | H | H | O | O | NH | 1 | Ph | Ph |
| —N(CH₃)₂ | H | p-tolyl-SO₂- | OH | H | H | H | Bond | O | NH | 1 | Ph | Ph |
| —N(CH₃)₂ | H | H | OH | H | H | H | O | O | NH | 1 | Ph | Ph |
| OH | H | H | OH | H | H | H | O | O | NH | 1 | Ph | Ph |
| —OCH₂Ph | H | H | OH | H | H | H | O | O | NH | 1 | Ph | Ph |
| —N(CH₃)₂ | H | p-tolyl-SO₂- | OH | H | H | H | O | O | NH | 1 | Ph | Pyridyl |
| —N(CH₃)₂ | H | p-tolyl-SO₂- | H | H | H | H | O | O | O | 1 | Ph | Pyridyl |
| N-acetylpiperazinyl | H | H | OH | H | H | H | O | O | NH | 1 | Ph | Ph |
| morpholinyl | H | H | OH | H | H | H | O | O | NH | 1 | Ph | Pyridyl |
| —N(CH₃)₂ | H | H | H | H | H | H | O | O | NH | 1 | Ph | Pyridyl |

-continued
(I)
| R¹ | R² | R³ | R⁶ | R⁴ | R⁵ | R⁷ | X | Y | Z | n | A | B |
|---|---|---|---|---|---|---|---|---|---|---|---|---|
| —N(CH₃)₂ | H | H | H | H | H | H | O | O | O | 1 | Ph | 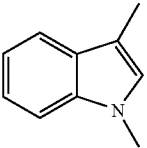 |
| —N(CH₃)₂ | H | H | H | H | H | H | Bond | O | NH | 1 | Ph | Ph |
| —N(CH₃)₂ | H | H | OH | H | H | H | O | O | NH | 1 | Ph | 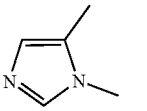 |
| —N(CH₃)₂ | H | H | OH | H | H | H | O | O | NH | 1 | Ph | 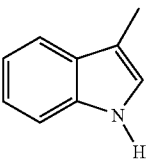 |
| —NH₂ | H | H | OH | H | H | H | O | O | NH | 1 | Ph | 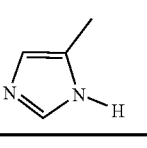 |
| —NH₂ | H | H | OH | H | H | H | O | O | NH | 1 | Ph |  |
A process for the preparation of compounds of the general formula (I) is provided by the following scheme I.
Scheme I
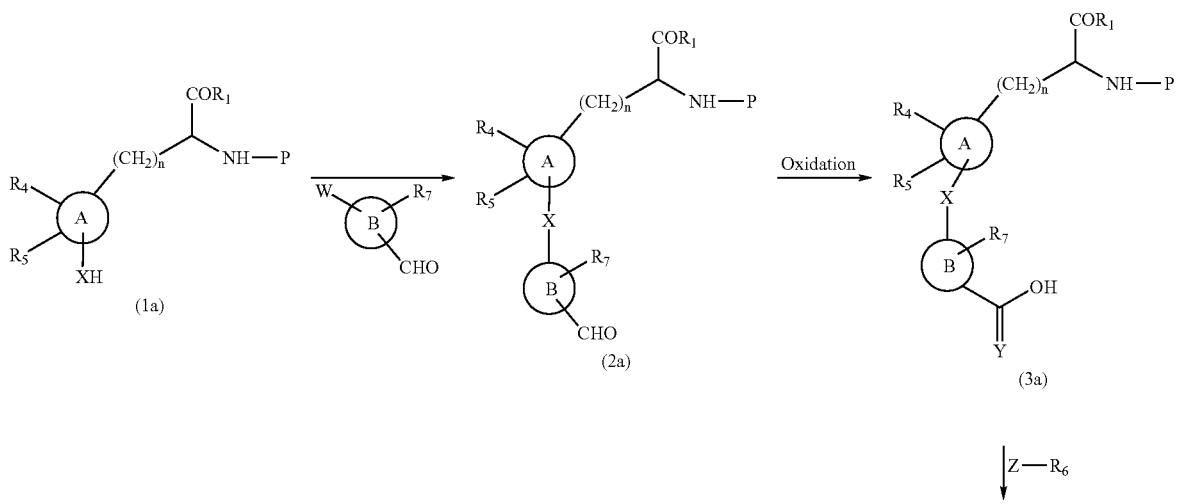

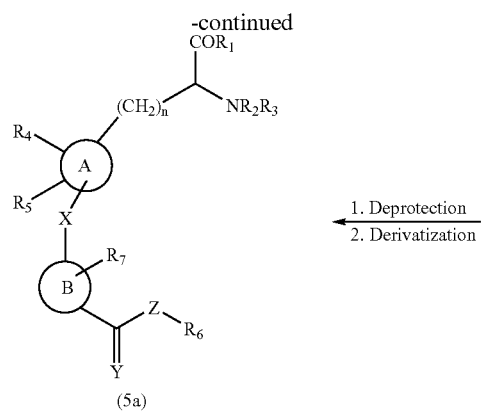 (5a)

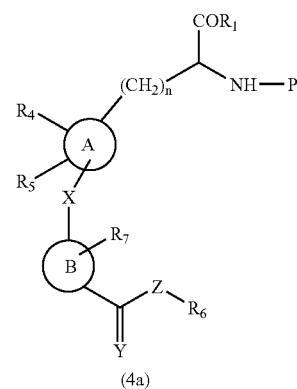 (4a)

The compound of the general formula (I) is prepared by the following procedure;

Step-(I): The condensation of amino acid derivative of compound of formula (1a), (wherein P represents protecting group) with substituted halo-aryl aldehyde (W=halo) is carried out in the presence of solvents selected from toluene, DMF, tetrahydrofuran, chloroform, dichloromethane, dichloroethane, ethyl acetate, o-dichlorobenzene or a mixture thereof, in the presence of base such as triethyl amine, diethylamine, pyridine, DMAP, alkali hydroxides, alkaline earth metal hydroxide, alkali carbonates such as sodium hydroxide, potassium hydroxide, potassium carbonate and the like to get the compound of formula (2a). The reaction is carried out at a temperature in the range of room temperature to reflux temperature 0° C. to 100° C.

Step-(II): The free aldehyde on the compound of the formula (2a) is oxidized with an oxidizing agent such as potassium permanganate and the like, in the presence of solvents THF and water to produce the compound of the formula (3a).

Step-(III): For making an amide (Z=N), the compound of formula (3a) is reacted with $H_2N-R_6$ wherein $R_6$ is as described above in the presence of reagents selected from dicyclohexylcarbodiimide (DCC), N-hydroxysuccinimide (NHS), benzotriazol-1-yloxy-tris(dimethylamino)phosphonium hexafluorophosphate (BOP), 1-ethyl-3-(3-dimethylaminopropyl)carbodiimide (EDAC), 1-hydroxybenztriazole hydrate (HOBt) in the presence of base such as triethyl amine, pyridine, DMAP, and the like and solvents such as toluene, methanol, ethanol, tetrahydrofuran, chloroform, dichloromethane, dichloroethane, ethylacetate, o-dichlorobenzene or a mixture thereof to produce the compound of the formula (4a). For making an ester (Z=O) or thioester (Z=S), a suitable activated acid form of the compound of formula (3a) is used, such as an activated ester or acid halide, to react with $Z-R_6$.

Step-(IVa): The deprotection of compound of formula (4a) may be carried out using Pd/C or HCl in the presence of solvents. Alternatively, the deprotection may also be carried out by passing HCl gas in the presence of solvent selected from acetonitrile, dichloromethane, methanol, dimethylsulfoxide, dimethylformamide, tetrahydrofuran, trifluoro acetic acid, 1-methyl-2-pyrrolidinone, N,N-dimethylacetamide and the like or mixtures thereof.

Step-(IVb): The deprotected amide nitrogen is derivatized with $R_2$ and/or $R_3$ by conventional methods.

It is appreciated that in any of the above-mentioned reactions, any reactive group in the substrate molecule may be protected according to chemical practice. Suitable protecting groups in any of the above-mentioned reactions are those used in the art. The methods of formation and removal of such protecting groups are those methods appropriate to the molecule being protected. The protecting group P used in the invention are protecting groups such as t-butoxy carbonyl (t-Boc), trityl, trifluoroacetyl, benzyloxy, benzyloxy carbonyl (Cbz) and the like.

The pharmaceutically acceptable salts are prepared by reacting the compound of formula (I) with 1 to 4 equivalents of a base such as sodium hydroxide, sodium methoxide, sodium hydride, potassium t-butoxide, calcium hydroxide, magnesium hydroxide and the like, in solvents like ether, THF, methanol, t-butanol, dioxane, isopropanol, ethanol etc. Mixtures of solvents may be used. Organic bases such as lysine, arginine, diethanolamine, choline, guanidine and their derivatives may also be used. Alternatively, acid addition salts are prepared by treatment with acids such as hydrochloric acid, hydrobromic acid, nitric acid, sulfuric acid, phosphoric acid, p-toluenesulfonic acid, methanesulfonic acid, acetic acid, citric acid, maleic acid, salicylic acid, hydroxynaphthoic acid, ascorbic acid, palmitic acid, succinic acid, benzoic acid, benzene sulfonic acid, tartaric acid and the like in solvents like ethyl acetate, ether, alcohols, acetone, THF, dioxane etc. Mixture of solvents may also be used.

The present invention also provides a pharmaceutical composition, containing one or more of the compounds of the general formula (I) as defined above, their tautomeric forms, their derivatives, their analogues, their stereoisomers, their polymorphs, their pharmaceutically acceptable salts, their pharmaceutically acceptable solvates in combination with a pharmaceutically acceptable carrier, diluent and the like.

The pharmaceutical composition may be in the forms normally employed, such as tablets, capsules, powders, syrups, solutions, suspensions and the like. It may contain flavorants, sweeteners, etc. in suitable solid or liquid carriers or diluents, or in suitable sterile media to form injectable solutions or suspensions. Such compositions typically contain from 1 to 25%, preferably 1 to 15% by weight of active compound, the remainder of the composition being pharmaceutically acceptable carriers, diluents, excipients or solvents.

Suitable pharmaceutically acceptable carriers include solid fillers or diluents and sterile aqueous or organic solutions. The active compound will be present in such pharmaceutical compositions in the amounts sufficient to provide the desired dosage in the range as described above. Thus, for oral administration, the compounds can be combined with a suitable solid or liquid carrier or diluent to form capsules, tablets, powders, syrups, solutions, suspensions and the like. The pharmaceutical compositions, may, if desired, contain additional components such as flavourants, sweeteners, excipients and the like. For parenteral administration, the compounds can be combined with sterile aqueous or organic media to form injectable solutions or suspensions. For example, solutions in sesame or peanut oil, aqueous propylene glycol and the like can be used, as well as aqueous solutions of water-soluble pharmaceutically-acceptable acid addition salts or alkali or alkaline earth metal salts of the compounds. The injectable solutions prepared in this manner can then be, administered intravenously, intraperitoneally, subcutaneously, or intramuscularly, with intramuscular administration being preferred in humans.

Pharmaceutical composition of the present invention are useful for the treatment of inflammation and immunological diseases, particularly those mediated by cytokines such as TNF-α, IL-1, IL-6, IL-12 and cyclooxygenase such as COX-2 and for the treatment of disorders associated with insulin resistance, such as polycystic ovary syndrome, as well as hyperlipidemia, coronary artery disease, peripheral vascular disease and diabetes and related diseases.

These compounds are useful for treating or inhibiting inflammation or inflammatory diseases such as inflammatory collagen vascular diseases and arthritides, which are caused by, for example, cytokines or inducible enzymes such as TNF-alpha, IL-1, IL-6. The compounds are also helpful in IL-12 mediated immunomodulatory effects like asthma, airway inflammation, inflammatory bowel disease, psoriasis, multiple sclerosis and others.

The present invention is provided by the examples below, which are provided by way of illustration only and should not be considered to limit the scope of the invention.

EXAMPLE 1

Synthesis of 2-amino-3-[4-(4-hydroxycarbamoylphenoxy)-phenyl]-propionic acid benzyl ester hydrochloric acid salt (6)

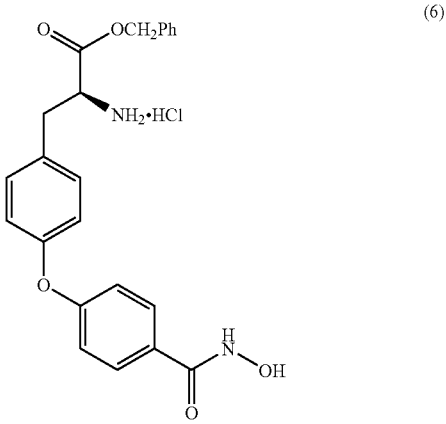

Step-I
Preparation of 2-tertbutoxycarbonylamino-3-[4-(4-formylphenoxy)-phenyl]-propionic acid (2)

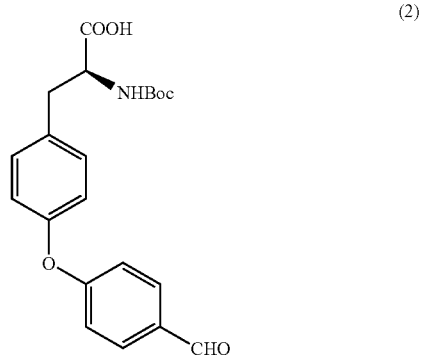

Potassium carbonate (14.74 g, 107 mmol) and 4-fluorobenzaldehyde (18.6 mL, 180 mmol) were added to a solution of amino acid (N-t-butoxycarbonyl-L-tyrosine) (10.0 g, 36 mmol) in anhydrous DMF (35 mL). The resulting suspension was refluxed at 75±5° C. under an atmosphere of argon. After 48 hr, the reaction mixture was cooled to room temperature, diluted with water (200 mL) and extracted with EtOAc (2×100 mL). The aqueous layer was collected, acidified with 5.0 M HCl to pH ~2.0 and extracted with EtOAc (2×150 mL). The resulting EtOAc layer was extracted with water (1×150 mL) and brine (1×150 mL), dried over anhydrous magnesium sulfate, filtered and concentrated under reduced pressure to yield the desired aldehyde as a low melting solid (13.7 g, ~99%). $^1$H NMR (300 MHz, DMSO-$d_6$): 9.89 (s, 1H), 7.82 (d, J=8.4 Hz, 2H), 7.23 (d, J=8.4 Hz, 2H), 7.00 (overlapped d, J=9.0 Hz, 4H), 4.63 (m, 1H), 3.2 (m, 1H), 3.06 (m, 1H), 1.40 (s, 9H).

Step II

Preparation of 2-tert-butoxycarbonylamino-3-[4-(4-formylphenoxy)-phenyl]-propionic acid benzyl ester (3)

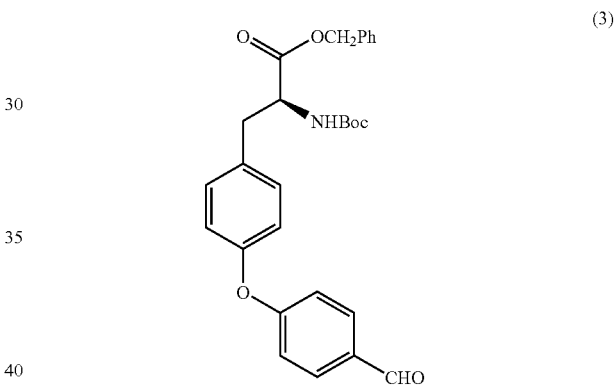

2-N-t-Butoxycarbonyl-3-[4-(4-formylphenoxy)phenyl)] propionic acid, 2, (4.3 g, 11.16 mmol) was dissolved in dichloromethane (30 mL) and cooled to 0-5° C. N,N'-Dicyclohexylcarbodiimide (3.0 g, 14.5 mmol), anhydrous benzyl alcohol (1.2 mL, 11.16 mmol) and finally 4-dimethylaminopyridine (0.27 g, 2.23 mmol) were added and the resulting mixture was stirred at that temperature under an atmosphere of argon. After 30 min, the reaction mixture was warmed up to room temperature and stirring was continued. After 2 h, the reaction mixture was cooled in an ice bath to precipitate out the side product N,N'-dicyclohexylurea that was filtered and the clear filtrate was concentrated under vacuum. The resulting oil was dissolved in ethyl acetate (2×100 mL), washed with 10% citric acid (1×100 mL), water (1×100 mL) and brine (1×100 mL), dried over anhydrous magnesium sulfate and concentrated under reduced pressure to yield the crude product. This crude material was purified by silica gel flash chromatography using toluene-ethyl acetate (93:7) mixture to yield the benzyl ester 3 (4.7 g, 88.6%). $^1$H NMR (DMSO-$d_6$): 9.91 (s, 1H), 7.89 (d, J=8.0 Hz, 2H), 7.42 (d, J=8.4 Hz, 2H), 7.31-7.43 (m, 7H), 7.06 (d, J=8.8 Hz, 2H), 7.05 (d, J=8.4 Hz, 2H), 5.12 (s, 2H), 4.23-4.29 (m, 1H), 3.05 (dd, J=13.6 and 5.2 Hz, 1H), 2.91 (dd, J=14.0 and 10.2 Hz, 1H), 1.33 (s, 9H).

Step III

Preparation of 4-[4-(2-benzyloxycarbonyl-2-tert-butoxycarbonylamino-ethyl)-phenoxy]-benzoic acid (4)

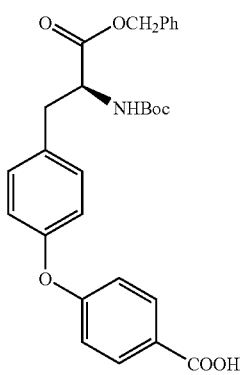

(4)

Benzyl ester 3 (4.6 g, 9.7 mmol) was dissolved in THF (100 mL) and the solution stirred at 70° C. Potassium permanganate (7.7 g, 48.5 mmol) dissolved in water (125 mL) was added slowly through a dropping funnel over a period of 2 hours. After addition was complete, reaction mixture was stirred at 70° C. for 30 min and cooled to room temperature. The brown precipitate was filtered over a Celite® bed and the filtrate was concentrated under reduced pressure. The residual oil was taken up in EtOAc (100 mL) and acidified with 2.0 M HCl. The organic layer was separated and washed with water (1×100 mL) and brine (1×100 mL), dried, and concentrated under reduced pressure to yield the desired acid compound 4 (4.5 g, 94%). $^1$H NMR (DMSO-$d_6$): 12.7 (br, 1H), 7.91 (d, J=8.8 Hz, 2H), 7.42 (d, J=8.4 Hz), 7.30-7.37 (m, 7H), 7.03 (d, J=8.8 Hz, 2H), 6.97 (d, J=8.8 Hz, 2H), 5.12 (s, 2H), 4.24-4.28 (m, 1H), 3.04 (dd, J=13.6 and 5.2 Hz, 1H), 2.91 (dd, J=13.6 and 9.6 Hz, 1H), 1.33 (s, 9H).

Step IV

Preparation of 2-tert-butoxycarbonylamino-3-[4-(4-hydroxycarbamoylphenoxy)-phenyl]-propionic acid benzyl ester (5)

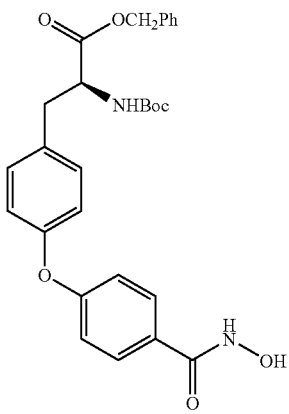

(5)

Acid compound 4 (1.1 g, 2.24 mmol) was dissolved in N,N-dimethylformamide (10 mL) and stirred under an atmosphere of argon. N-Methylmorpholine (1.0 mL, 8.96 mmol) was added, the reaction mixture was cooled to 0° C. and BOP reagent (1.09 g, 2.46 mmol) was added. After 20 min, hydroxylamine hydrochloride (0.31 g, 4.48 mmol) was added and the reaction mixture was warmed up to room temperature and stirred overnight. The solvent was removed under reduced pressure and residual material was partitioned between EtOAc (50 mL) and saturated $NH_4Cl$ solution (1×30 mL). The organic layer was dried and concentrated to yield the crude material. Flash chromatography on $SiO_2$ gel using hexanes-ethyl acetate (1:1) mixture containing 1% acetic acid furnished the desired hydroxamic acid compound 5 (0.5 g, 44%). $^1$H NMR (DMSO-$d_6$): 11.20 (br, 1H), 9.00 (br, 1H), 7.76 (d, J=8.8 Hz, 2H), 7.42 (d, J=8.0 Hz, 2H), 7.28-7.38 (m, 7H), 6.98 (overlapped d, J=8.4 Hz, 4H), 5.12 (s, 2H), 4.21-4.27 (m, 1H), 3.03 (dd, J=13.6 and 5.6 Hz, 1H), 2.89 (dd, J=10.0 and 14.0 Hz, 1H), 1.33 (s, 9H).

Step V

Preparation of 2-amino-3-[4-(4-hydroxycarbamoylphenoxy)-phenyl]-propionic acid benzyl ester hydrochloric acid salt (6)

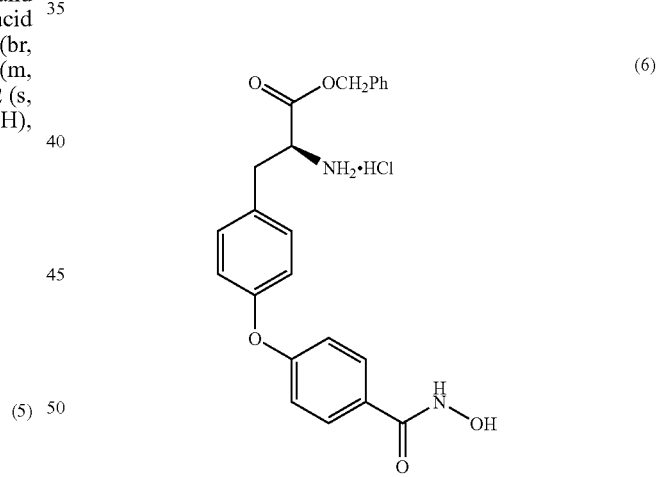

(6)

The hydroxamate 5 (0.4 g) was dissolved in $CH_2Cl_2$ and cooled to 0-5° C. Hydrogen chloride gas was bubbled through this solution for 20 min. The bubbling was discontinued and the reaction mixture was stirred at room temperature for 1 h. The excess HCl was degassed and the $CH_2Cl_2$ was removed. The residual solid was triturated with EtOAc (2×50 mL), decanted, and dried to yield the desired compound 6 as a white amorphous solid (0.25 g, 71.4%). $^1$H NMR (DMSO-$d_6$): 11.18 (s, 1H), 7.78 (d, J=8.8 Hz, 2H), 7.31-7.39 (m, 5H), 7.24 (d, J=8.4 Hz, 2H), 6.99 (d, J=8.4 Hz, 2H), 6.98 (d, J=8.8 Hz, 2H), 5.19 (s, 2H), 4.40 (m, 1H), 3.07-3.18 (m, 2H) LCMS (m/e): Obsd, 407.0; Calcd, 406.43.

EXAMPLE 2

Synthesis of 2-amino-3-[4-(4-hydroxycarbamoyl-phenoxy)-phenyl]-propionic acid hydrochloric acid salt (9)

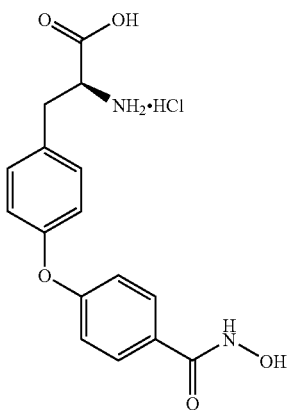
(9)

Step I

Preparation of 3-[4-(4-benzyloxycarbamoylphenoxy)-phenyl]-2-tert-butoxycarbonylamino-propionic acid benzyl ester (7)

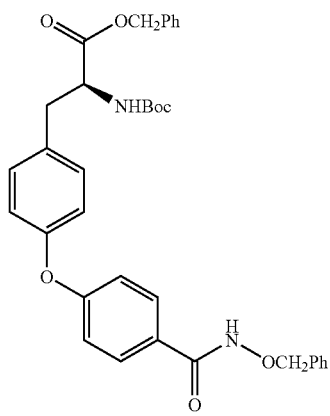
(7)

The acid compound 4 (0.6 g, 1.22 mmol) was dissolved in dry DMF (15 mL) and cooled to 0-5° C. 1-Hydroxybenzotriazole (0.18 g, 1.34 mmol), 1-(3-dimethylaminopropyl)-3-ethylcarbodiimide hydrochloride (0.23 g, 1.22 mmol), and triethylamine (0.6 mL, 3.66 mmol) were added to the above mixture followed by stirring for 15 min. O-Benzylhydroxylamine hydrochloride (0.22 g, 1.34 mmol) was added and the mixture was allowed to come to room temperature and stirred for 18 h. The solvent was evaporated under reduced pressure and the residual oil was taken up in EtOAc (50 mL). The organic layer was extracted with 2.0 M HCl (1×10 mL), saturated NaHCO$_3$ (1×10 mL), water (1×25 mL) and brine (1×25 mL). The resulting EtOAc layer was dried and concentrated to yield the crude product. Flash chromatography using hexanes-ethyl acetate (1:1) yielded the desired benzyl hydroxamate 7 (0.4 g, 56%). $^1$H NMR (DMSO-d$_6$): 11.73 (s, 1H), 7.75 (d, J=8.4 Hz, 2H), 7.29-7.47 (m, 13H), 6.99 (d, J=8.8 Hz, 2H), 6.99 (5.12 (s, 2H), 4.92 (s, 2H), 4.23-4.28 (m, 1H), 3.03 (dd, J=13.6 and 5.2 Hz, 1H), 2.90 (dd, J=13.6 and 10.0 Hz, 1H), 1.33 (s, 9H).

Step II

Preparation of 2-tert-butoxycarbonylamino-3-[4-(4-hydroxycarbamoyl-phenoxy)-phenyl]-propionic acid (8)

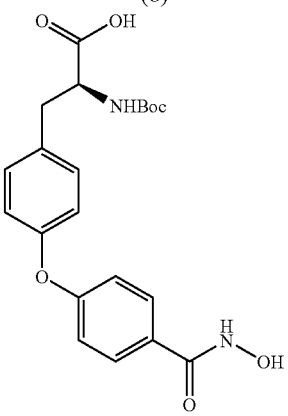
(8)

Palladium on carbon (5%, 0.3 g) was added to a degassed solution of the benzyl hydroxamate 7 (0.4 g) in MeOH (25 mL) and the suspension was treated with hydrogen at atmospheric pressure for 4 h. The suspension was filtered over a Celite® bed and concentrated to yield the desired hydroxamate 8 (0.2 g, 72%). $^1$H NMR (DMSO-d$_6$): 11.20 (s, 1H), 9.02 (br, 1H), 7.75 (d, J=8.8 Hz, 2H), 7.30 (d, J=8.8 Hz, 2H), 7.11 (d, J=8.8 Hz, 1H), 6.99 (d, J=8.8 Hz, 2H), 6.96 (d, J=8.8 Hz, 2H), 4.10 (ddd, J=12.8 10.0, and 4.4 Hz, 1H), 3.03 (dd, J=13.6 and 4.4 Hz, 1H), 2.82 (dd, J=13.6 and 10.4 Hz, 1H), 1.33 (s, 9H).

Step III

Preparation of 2-amino-3-[4-(4-hydroxycarbamoyl-phenoxy)-phenyl]-propionic acid hydrochloric acid salt (9)

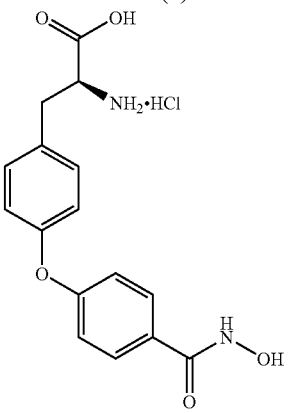
(9)

The hydroxamate 8 (0.2 g) was dissolved in CH$_2$Cl$_2$ and cooled to 0-5° C. Hydrogen chloride gas was bubbled through this solution for 20 min. The bubbling was discontinued and the reaction mixture was stirred at room temperature for 1 h. The excess HCl was degassed and the CH$_2$Cl$_2$ was removed. The residual solid was triturated with EtOAc (2×25 mL), decanted, and dried to yield the desired compound 9 as a white amorphous solid (0.17 g, quantitative yield). $^1$H NMR (360 MHz, DMSO-d$_6$): 11.15 (s, 1H), 8.96 (br, 1H), 7.77 (d, J=9.0 Hz, 2H), 7.32 (d, J=7.9 Hz, 2H), 7.04 (d, J=9.0 Hz, 2H), 6.99 (d, J=8.6 Hz, 2H), 4.16 (m, 1H), 3.09-3.14 (m, 2H). LCMS (m/e): Obsd. 317.0, Calcd. 316.31.

EXAMPLE 3

Synthesis of 4-[4-(2-amino-2-dimethylcarbamoyl-ethyl)-phenoxy]-N-hydroxybenzamide hydrochloric acid salt (13)

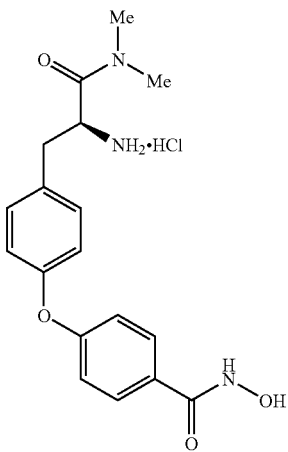

(13)

Step I

Preparation of {1-dimethylcarbamoyl-2-[4-(4-formylphenoxy)-phenyl]-ethyl}-carbamic acid tert-butyl ester (10)

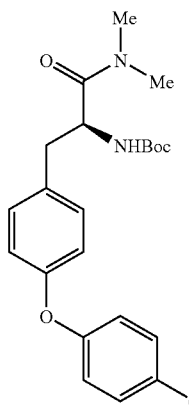

(10)

The aldehyde compound 2 (2.0 g, 5.2 mmol) was dissolved in CH$_2$Cl$_2$ (30 mL) and stirred at room temperature under an atmosphere of argon. Triethylamine (0.87 mL, 6.23 mmol) and BOP reagent (2.53 g, 5.7 mmol) were added and the reaction mixture was stirred for 15 min. Dimethylamine (2.0 M solution in THF, 13.0 mL, 26.0 mmol) was added and the resulting solution was stirred at room temperature for about 2-3 h. The solvent was removed under reduced pressure and the resulting oil was taken up in EtOAc (100 mL). The organic layer was extracted with 0.5 N NaOH (1×10 mL), water (2×50 mL) and brine (1×50 mL). Drying and concentration of the organic layer gave the desired amide 10 (2.1 g, ~98%). $^1$H NMR (400 MHz, DMSO-d$_6$): 9.91 (s, 1H), 7.90 (d, J=8.8 Hz, 2H), 7.35 (d, J=8.4 Hz, 2H), 7.15 (d, J=8.4 Hz, 1H), 7.06 (d, J=8.8 Hz, 2H), 7.05 (d, J=8.4 Hz, 2H), 4.57 (m, 1H), 2.94 (s, 3H), 2.75-2.91 (m, 5H), 1.31 (s, 9H).

Step II

Preparation of 4-[4-(2-tert-butoxycarbonylamino-2-dimethylcarbamoyl-ethyl)-phenoxy]-benzoic acid (11)

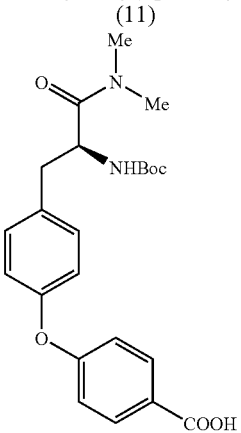

(11)

Amide compound 10 (2.0 g, 4.85 mmol) was dissolved in THF (50 mL) and the solution stirred at 70° C. Potassium permanganate (3.06 g, 19.4 mmol) dissolved in water (50 mL) was added slowly through a dropping funnel (5 mL/min) over 2 hours. After addition was complete, reaction mixture was stirred at 70° C. for 30 min and cooled to room temperature. The brown precipitate was filtered over a Celite® bed and the filtrate was concentrated under reduced pressure. The residual oil was taken up in EtOAc (100 mL) and acidified with 2.0 M HCl. The organic layer was separated and washed with water (1×50 mL) and brine (1×50 mL), dried, and concentrated under reduced pressure to yield the desired acid compound 11 (1.9 g, 91%). $^1$H NMR (DMSO-d$_6$): 12.7 (br, 1H), 7.91 (d, J=8.8 Hz, 2H), 7.33 (d, J=8.4 Hz, 2H), 7.13 (d, J=8.8 Hz, 1H), 7.04 (d, J=8.4 Hz, 2H), 6.96 (d, J=8.8 Hz, 2H), 4.56 (ddd, J=13.6, 9.2, and 6.0 Hz, 1H), 2.93 (s, 3H), 2.74-2.91 (m, 5H), 1.31 (s, 9H).

Step III

Preparation of {1-dimethylcarbamoyl-2-[4-(4-hydroxycarbamoyl-phenoxy)-phenyl]-ethyl}-carbamic acid tert-butyl ester (12)

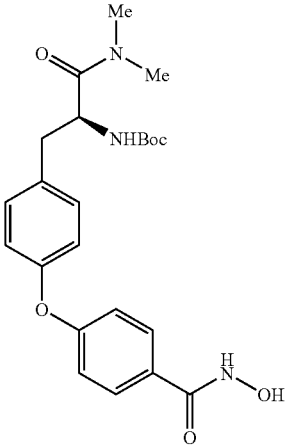

(12)

Acid compound 11 (1.9 g, 4.43 mmol) was dissolved in N,N-dimethylformamide (20 mL) and stirred under an atmosphere of argon. N-Methylmorpholine (1.95 mL, 18.0 mmol) was added, the reaction mixture was cooled to 0° C. and BOP reagent (2.16 g, 4.88 mmol) was added. After 20 min, hydroxylamine hydrochloride (0.62 g, 8.87 mmol) was added and the reaction mixture was warmed up to room temperature and stirred overnight. The solvent was removed under reduced pressure and residual material was partitioned between EtOAc (50 mL) and saturated NH$_4$Cl solution (1×30 mL). The organic layer was dried and concentrated to yield the crude material. Flash chromatography over silica gel using chloroform-methanol (19:1) yielded the desired hydroxamic acid compound 12 (0.9 g, 46%). $^1$H NMR (DMSO-d$_6$): 8.95 (br, 1H), 7.73 (d, J=9.2 Hz, 2H), 7.28 (d, J=8.4 Hz, 2H), 7.18 (d, J=8.4 Hz, 1H), 7.00 (d, J=8.8 Hz, 2H), 6.95 (d, J=8.8 Hz, 2H), 4.55 (m, 1H), 2.91 (s, 3H), 2.70-2.90 (m, 5H), 1.30 (s, 9H).

Step IV

Preparation of 4-[4-(2-amino-2-dimethylcarbamoyl-ethyl)-phenoxy]-N-hydroxybenzamide hydrochloric acid salt (13)

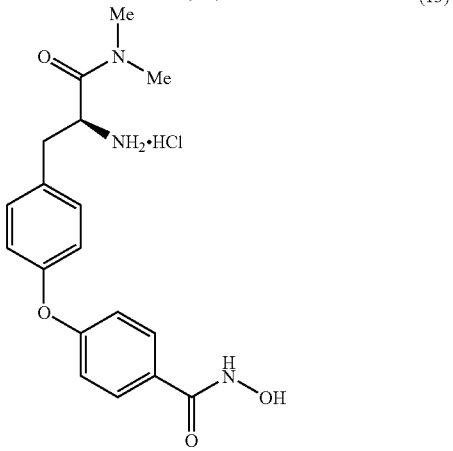

(13)

The hydroxamate 12 (0.8 g) was dissolved in CH$_2$Cl$_2$ (25 mL) and cooled to 0-5° C. Hydrogen chloride gas was bubbled through this solution for 20 min. The bubbling was discontinued and the reaction mixture was stirred at room temperature for 1 h. The excess HCl was degassed and the CH$_2$Cl$_2$ was removed. The residual solid was triturated with EtOAc (2×25 mL), decanted, and dried to yield the desired compound 13 as a white amorphous solid (0.34 g,). $^1$H NMR (DMSO-d$_6$): 11.20 (s, 1H), 7.76 (d, J=8.8 Hz, 2H), 7.24 (d, J=8.8 Hz, 2H), 7.02 (d, J=8.4 Hz, 2H), 6.95 (d, J=8.8 Hz, 2H), 4.52 (m, 1H), 2.92-3.05 (m, 1H), 2.76 (s, 3H), 2.71 (s, 3H). LCMS: Obsd 344.0, calcd 343.48.

EXAMPLE 4

4-{4-[2-Dimethylcarbamoyl-2-(toluene-4-sulfonylamino)-ethyl]-phenoxy}-N-hydroxy-benzamide (14)

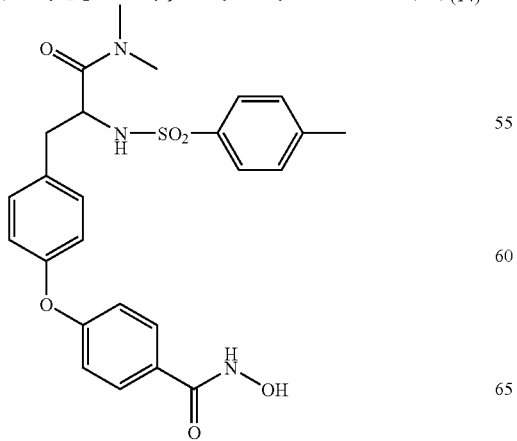

(14)

The title compound is a low melting solid. $^1$H NMR (DMSO-d$_6$): 11.90 (br, 1H), 11.14 (br, 1H), 8.98 (s, 1H), 7.76 (d, J=9.2 Hz, 2H), 7.55 (d, J=8.0 Hz, 2H), 7.30 (d, J=8.0 Hz, 2H), 7.17 (d, J=8.4 Hz, 2H), 6.95 (d, J=7.2 Hz, 2H), 6.93 (d, J=7.2 Hz, 2H), 4.32 (m, 1H), 2.81 (dd, J=13.2 and 7.2 Hz, 1H), 2.71 (s, 3H), 2.64 (dd, J=13.2 and 8.0 Hz, 1H), 2.53(s, 3H), 2.35 (s, 3H).

EXAMPLE 5

4-[4-(2-Amino-2-isopropoxycarbonylethyl)-phenoxy]-benzoicacid (15)

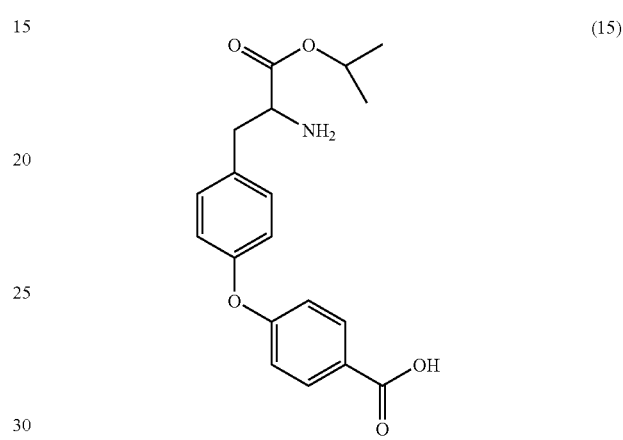

(15)

The title compound 15 was isolated as white solid. $^1$H NMR (DMSO-d$_6$): 7.93 (d, J=8.8 Hz, 2H), 7.33 (d, J=8.8 Hz, 2H), 7.09 (d, J=8.4 Hz, 2H), 7.05 (d, J=8.4 Hz, 2H), 4.92 (m, 1H), 4.22 (m, 1H), 3.19 (dd, J=14.0 and 6.0 Hz, 1H), 3.06 (dd, J=14.0 and 8.0 Hz, 1H), 1.18 (d, J=6.4 Hz, 3H), 1.09 (d, J=6.4 Hz, 3H).

EXAMPLE 6

2-Amino-3-[4-(4-hydroxycarbamoylphenoxy)-phenyl]-propionic acid isopropyl ester (16)

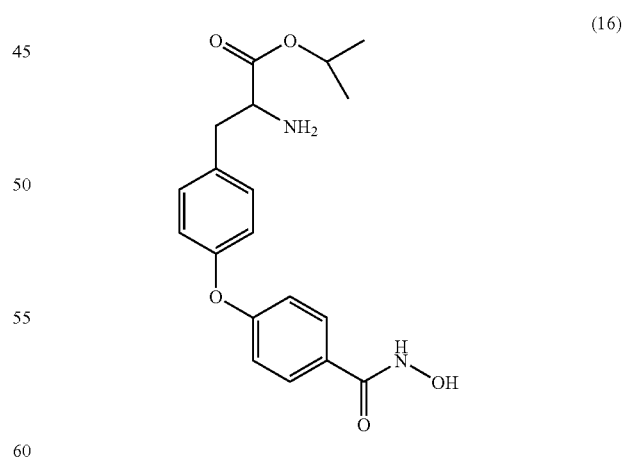

(16)

The title compound 16 was isolated as white solid. $^1$H NMR (DMSO-d$_6$): 11.16 (br, 1H), 7.78 (d, J=8.8 Hz, 2H), 7.31 (d, J=8.4 Hz, 2H), 7.06 (d, J=8.8 Hz, 2H), 6.98 (d, J=8.8 Hz, 2H), 4.92 (m, 1H), 4.22 (m, 1H), 3.18 (dd, J=14.0 and 6.0 Hz, 1H), 3.06 (dd, J=14.0 and 8.0 Hz, 1H), 1.18 (d, J=6.4 Hz, 3H), 1.08 (d, J=6.4 Hz, 3H).

EXAMPLE 7

Synthesis of L-6-[4-(2-amino-2-dimethylcarbamoyl-ethyl)-phenoxy]-N-hydroxy-nicotinamide hydrochloride (21)

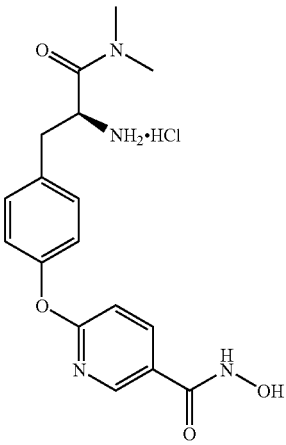

(21)

Step I

Preparation of 6-[4-(2-tert-butoxycarbonylamino-2-carboxy-ethyl)-phenoxy]-nicotinic acid methyl ester (17)

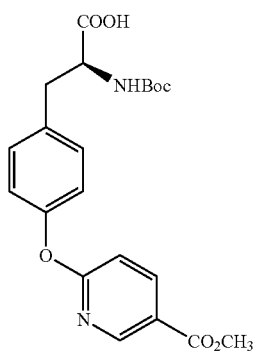

(17)

Potassium carbonate (1.23 g, 8.9 mmol) and methyl 6-chloronicotinate (1.8 g, 10.66 mmol) were added to a solution of Boc-tyrosine (1.0 g, 3.55 mmol) in anhydrous DMF (15 mL). The resulting suspension was refluxed at 70 deg C. under an atmosphere of argon. After 72 hrs, the reaction mixture was cooled to room temperature, diluted with water (100 mL) and extracted with EtOAc (2×100 mL). The aqueous layer was collected, acidified with 5.0 M HCl to pH ~2.5 and extracted with EtOAc (2×100 mL). The resulting EtOAc layer was extracted with water (1×150 mL) and brine (1×150 mL), dried over anhydrous magnesium sulfate, filtered and concentrated and flash chromatographed (30-40% ethyl acetate in hexane with 1% acetic acid) to yield desired ester, 17 as a solid (1.4 g). $^1$H NMR (400 MHz, DMSO-d$_6$): 12.45 (s, 1H), 8.68 (br, 1H), 8.29 (dd, J=8.4 and 2.4 Hz, 1H), 7.31 (d, J=8.4 Hz, 2H), 7.14 (d, J=8.8 Hz, 1H), 7.08 (m, 3H), 4.12 (m, 1H), 3.85 (s, 3H), 3.05 (dd, J=14.0 and 4.0 Hz, 1H), 2.84 (dd, J=14.0 and 10.8 Hz, 1H) 1.33 (s, 9H)

Step II

Preparation of 6-[4-(2-tert-butoxycarbonylamino-2-dimethylcarbamoyl-ethyl)-phenoxy]-nicotinic acid methyl ester (18)

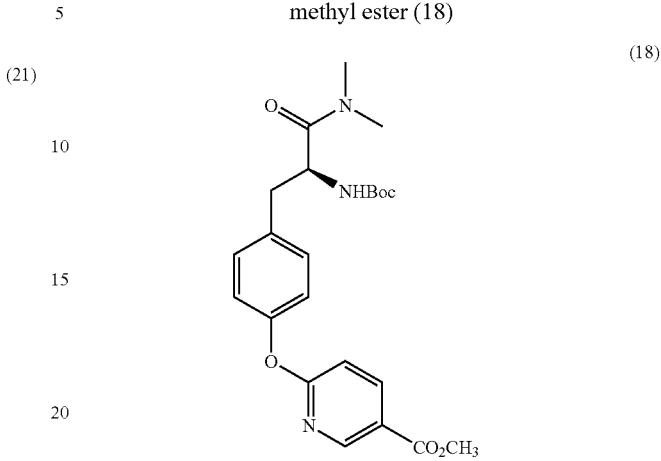

(18)

The compound 17 (2.2 g, 5.28 mmol) was dissolved in CH$_2$Cl$_2$ and stirred at room temperature under an atmosphere of argon. Triethylamine (0.883 mL, 6.33 mmol) and benzotriazol-1-yloxy-tris(dimethylamino)phosphonium hexafluorophosphate (BOP reagent, 2.5 g, 5.80 mmol) were added and the reaction mixture was stirred for 15 min. Dimethylamine (2.0 M solution in THF, 13.2 mL, 26.4 mmol) was added and the resulting solution was stirred at room temperature for about 2-3 h. The solvent was removed under reduced pressure and the resulting oil was taken up in EtOAc (200 mL). The organic layer was extracted with 0.5 N NaOH (1×30 mL), water (2×100 mL) and brine (1×100 mL). Drying and concentration of the organic layer gave the desired amide 18 (1.3 g, ~98%). $^1$H NMR (400 MHz, DMSO-d$_6$): 8.67 (br, 1H), 8.29 (dd, J=8.8 and 2.4 Hz, 1H) 7.31 (d, J=8.4 Hz, 2H), 7.11 (d, J=8.8 Hz, 1H), 7.08 (m, 3H), 4.57 (m, 1H), 3.85 (s, 3H), 2.93 (s, 3H), 2.85-2.75 (m, 2H), 2.80 (s, 3H), 1.32 (s, 9H).

Step III

Preparation of 6-[4-(2-tert-butoxycarbonylamino-2-dimethylcarbamoyl-ethyl)-phenoxy]-nicotinic acid (19)

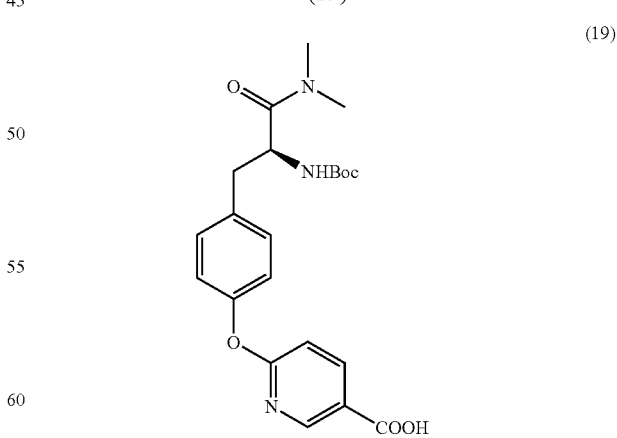

(19)

Amide 18 (1.0 g, 2.25 mmol) was dissolved in THF (10 mL) and diluted with water (10 mL). Lithium hydroxide (0.107 g, 4.5 mmol) was added and the reaction mixture was stirred at room temperature for about 2 h. The THF was evaporated and the resulting aqueous layer was acidified with 2.0 M HCl and extracted into EtOAc (2×100 mL). The organic layer was washed with water (1×100 mL) and brine (1×100 mL), dried and concentrated to yield the desired acid compound 19 (1.0 g, 97%). $^1$H NMR (400 MHz, DMSO-d$_6$): 13.1 (s, 1H), 8.64 (br, 1H), 8.27 (dd, J=8.4 and 2.0 Hz, 1H), 7.30 (d, J=8.4 Hz, 2H), 7.11 (d, J=8.8 Hz, 1H), 7.08 (m, 3H), 4.56 (m, 1H), 2.94 (s, 3H), 2.85-2.75 (m, 2H), 2.81 (s, 3H), 1.18 (s, 9H).

Step IV
Preparation {1-dimethylcarbamoyl-2-[4-(5-hydroxy-carbamoyl-pyridin-2-yloxy)-phenyl]-ethyl}-carbamic acid tert-butyl ester (20)

(20)

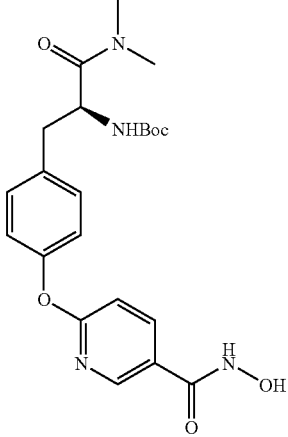

The acid compound 19 (1.0 g, 2.328 mmol) was dissolved in dry DMF and stirred under an atmosphere of argon. N-Methylmorpholine (1.02 mL, 9.32 mmol) was added. After 20 min, hydroxylamine hydrochloride (0.323 g, 4.66 mmol) was added and the reaction mixture was warmed up to room temperature and stirred overnight. The solvent was removed under reduced pressure and residual material was partitioned between EtOAc (50 mL) and saturated NH4Cl solution (1×30 mL). The organic layer was dried and concentrated to yield the crude material. Flash chromatography on SiO$_2$ gel using hexanes-ethyl acetate (70-60%) mixture containing 1% acetic acid furnished the desired hydroxamic acid compound 20 (0.5 g, 98%) $^1$H NMR (400 MHz, DMSO-d$_6$): 8.47 (br, 1H) 8.14 (dd, J=8.8 and 2.4 Hz, 1H), 7.29 (d, J=8.4 Hz, 2H), 7.11 (d, J=8.8 Hz, 1H), 7.05 (m, 3H), 4.56 (m, 1H), 2.93 (s, 3H) 2.85-2.75 (m, 2H), 2.79 (s, 3H), 1.32 (s, 9H)

Step V
Preparation of L-6-[4-(2-amino-2-dimethylcarbamoylethyl)-phenoxy]-N-hydroxynicotinamide hydrochloride (21)

(21)

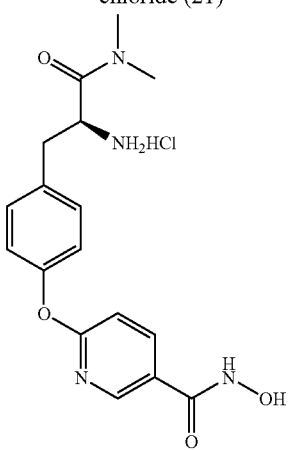

The hydroxamate 20 (0.5 g) was dissolved in CH$_2$Cl$_2$ and cooled to 0-5° C. Hydrogen chloride gas was bubbled through this solution for 20 min. The bubbling was discontinued and the reaction mixture was stirred at room temperature for 1 h. The excess HCl was degassed and the CH$_2$Cl$_2$ was removed. The residual solid was titurarted with EtOAc (2×50 mL), decanted, and dried to yield the desired compound 21 as a white amorphous solid (0.4 g, 98%). $^1$H NMR (DMSO-d$_6$): 8.49 (d, J=2.4 Hz, 1H), 8.31 (br, 2H), 8.17 (dd, J=8.8 and 2.4 Hz, 1H), 7.40 (br, 1H), 7.27 (d, J=8.4 Hz, 2H), 7.13 (d, J=8.4 Hz, 2H), 7.07 (d, J=8.8 Hz, 1H), 4.58 (br, 1H), 3.08 (dd, J=13.6 and 6 Hz, 1H), 2.98 (dd, J=14.0 and 7.6 Hz, 1H), 2.81(s, 3H), 2.73(s, 3H).

EXAMPLE 8

Synthesis of 2-amino-3-[4-(4-hydroxycarbamoyl-phenoxy)-phenyl]-propionic acid sodium salt (22)

(22)

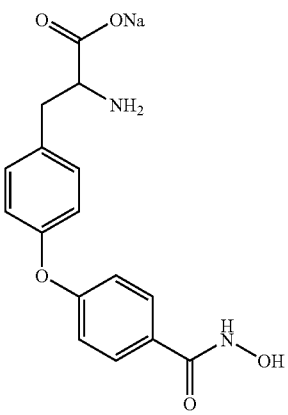

The compound 35 (0.3 g, 0.85 mmol) was dissolved in aqueous sodium hydroxide (1M, 1.7 mL). Water was removed under reduced pressure at 30° C. in CentriVap to yield compound 85 as a white amorphous solid (0.33 g, quantitative). $^1$H NMR (400 MHz, DMSO-d$_6$+DCI): 7.88(d, J=8.8 Hz, 2H), 7.31 (d, J=8.4 Hz, 2H), 7.01 (d, J=8.4 Hz, 2H), 6.96 (d, J=8.8 Hz, 2H), 4.13 (t, J=6.4 Hz, 1H), 3.13 (d, J=6.4 Hz, 2H). LCMS: Obsd. 339, Calcd. 338.3

Protocols for Biological Testing:

Compounds of the present invention have been tested for lowering inflammatory cytokines level, chemically induced inflammation, immunomodulation and blood glucose, in different models for their biological activity. The attached FIGS. 1-9 shows the activity profile of representative compounds of the invention.

Table I. Compounds Showing Inhibition of Major Pro-Inflammatory Cytokines in THP-1 Cells Human THP-1 monocyte cells were cultured and incubated with compounds at different concentrations. Cells were then challenged with lipopolysaccharides (LPS) at a concentration of (1 μg/mL) for 24 hours. Cell supernatants were then analyzed for the presence of TNF-α cytokines by antibody directed enzyme-linked immunoassay from R & D System, Minneapolis, USA. As shown in Table I, the representative compounds can inhibit the production of three major pro-inflammatory cytokines in a dose dependent mainer. No significant change in cell viability was observed with incubation of cells in the presence of highest concentration of the compound.

Table II. Compounds Showing Inhibition of Major Pro-Inflammatory Cytokines in Human Peripheral Mononuclear (hPBMC) Cells Human PBMC monocyte cells were cultured and incubated with compounds at different concentrations. Cells were then challenged with lipopolysaccharides (LPS) at a concentration of (1 µg/mL) for 24 hours. Cell supernatants were then analyzed for the presence of TNF-α, IL-6 and IL-1β cytokines by antibody directed enzyme-linked immunoassay. Dexamethasone was used as a positive control in the experiments. As shown in Table II, the compounds can inhibit the production of three major pro-inflammatory cytokines in a dose dependent manner. No significant change in cell viability was observed with incubation of cells in the presence of highest concentration of the compound.

Table III. Inhibition of TNF-α and IL-6 in LPS Induced Sepsis Model in Mice

SW mice were orally treated with vehicle, dexamethasone (5 mg/kg) and compounds at a dose of 50 mg/kg body weight one hour before LPS injection (10 µg/mouse, ip) and blood was collected after 90 min and measured serum TNF-α and IL-6 levels by ELISA. The compounds significantly lowered TNF-α and IL-6 in this model.

Table IV. Effect of Compounds in TACE, MMP-1, MMP-9, PDE-3 and PDE-4

The matrix metalloprotenase (MMP) family shares significant sequence homology and a common multidomain structure. On the basis of their preferred substrates, they can be divided into four main classes: collagenases, gelatinases, stromelysins and membrane-type MMPs. These enzymes demonstrate very low activity in normal tissue but are upregulated and/or activated during inflammation and physiological remodeling processes in response to specific stimuli, including cytokines, growth factors and extracellular matrix interactions. Inhibitors may be useful for cancer, rheumatoid arthritis, autoimmune diseases, periodontitis, tissue ulceration, atherosclerosis, aneurysm and heart failure.

MMP-1

The enzyme MMP-1 (interstitial collagenase; EC 3.4.24.7, human rheumatoid synovial fibroblast, Calbiochem Cat. 444208) is used. MMP-1 is first activated with APMA for 60 minutes at 37° C. Test compound and/or vehicle is then pre-incubated for 60 minutes at 37° C. with the active enzyme (8 µM) in a reaction mixture containing 50 mM MOPS (pH 7.2), 10 mM $CaCl_2$ and 10 µM $ZnCl_2$. The reaction is initiated by addition of Mca-Pro-Leu-Gly-Leu-Dpa-Ala-Arg-$NH_2$ (SEQ. ID NO. 1) (4 µM) and incubated for 120 minutes at 37° C. The N-terminal protecting group Mca is 7-methoxycoumarin-4-yl acetyl. The amino acid Dpa is $N^3$-(2,4-dinitrophenyl)-L-diaminopropanoyl. Enzyme activity is determined spectrofluorometrically by measuring the formation of fluorescent Mca-Pro-Leu-Gly (SEQ. ID NO. 2). Compounds are screened at 10 µM.

MMP-9

The enzyme MMP-9 (gelatinase B; EC 3.4.24.35, human recombinant, Calbiochem Cat. PF024-5UG) is used. MMP-9 is first activated with APMA for 60 minutes at 37° C. Test compound and/or vehicle is then preincubated for 60 minutes at 37° C. with the active enzyme (11 nM) in a reaction mixture containing 50 mM MOPS (pH 7.2), 10 mM $CaCl_2$ and 10 µM $ZnCl_2$. The reaction is initiated by addition of 4 µM Mca-Pro-Leu-Gly-Leu-Dpa-Ala-Arg-$NH_2$ (SEQ. ID NO. 1) and incubated for 120 minutes at 37° C. Enzyme activity is determined spectrofluorometrically by measuring the formation of fluorescent Mca-Pro-Leu-Gly (SEQ. ID NO. 2). Compounds are screened at 10 µM.

TACE

Tumor necrosis factor-α converting enzyme (TACE/ADAM-17) is responsible for the release of TNF-α, a potent proinflammatory cytokine associated with many chronic debilitating diseases such as rheumatoid arthritis and multiple sclerosis. TNF-α also induces angiogenesis, promotes fibroblast proliferation and can combine with receptors on selected tumor cells to induce cell lysis. TACE is also implicated in amyloid precursor protein secretion. Human recombinant TACE expressed in Sf21 cells (R&D System, 930-ADB) is used. Test compound and/or vehicle is incubated with the enzyme (25 ng/ml) and 10 µM Mca-P-L-A-Q-A-V-Dpa-R-S-S-S-R-$NH_2$ (SEQ. ID NO. 3) in Modified Tris-buffer pH 9.0 for 30 minutes at 25° C. Enzyme activity is determined spectrofluorimetrically by measuring the formation of fluorescent Mca-P-L-A-Q-A-$NH_2$ (SEQ. ID NO. 4). Compounds are screened at 10 µM.

PDE-3

Phosphodiesterase type-3 (PDE3) partially purified from human platelets is used. Test compound and/or vehicle is incubated with 1 µg enzyme and 1 µM cAMP containing 0.01 µM [$^3$H]cAMP in Tris buffer pH 7.5 for 20 minutes at 25° C. The reaction is terminated by 2 minutes boiling. The resulting AMP is converted to adenosine by addition of 10 mg/ml snake venom nucleotidase and further incubation at 37° C. for 10 minutes. Unhydrolyzed cAMP is bound to AG1-X2 resin, and remaining [$^3$H]Adenosine in the aqueous phase is quantitated by scintillation counting. Compounds are screened at 10 µM.

PDE-4

Phosphodiesterase type 4 (PDE4) catalyzes the conversion of cAMP or cGMP to their respective monophosphate forms. PDE4 is insensitive to $Ca^{2+}$/calmodulin or cGMP regulation, exhibits a cAMP substrate dependence, and is inhibited by the specific inhibitor Ro-20-1724. Since cyclic nucleotides are important second messengers in the cells of many tissues and organs, development of therapeutics that selectively target specific PDE isoforms is considered an important goal. PDE4 is believed to be the most important PDE isoform in bronchial relaxation, allergy and inflammation. Inhibitors selective for PDE4 may, therefore, be useful in the treatment of asthma, allergy and inflammatory disease. PDE4 partially purified from human U-937 myeloid leukemia cells is used. Test compound and/or vehicle is incubated with 0.2 µg enzyme and 1 µM cAMP containing 0.01 µM [$^3$H]cAMP in Tris buffer pH 7.5 for 20 minutes at 25° C. The reaction is terminated by boiling for 2 minutes and the resulting AMP is converted to adenosine by addition of 10 mg/ml snake venom nucleotidase and further incubation at 37° C. for 10 minutes. Unhydrolyzed cAMP is bound to AG1-X2 resin, and remaining [$^3$H] Adenosine in the aqueous phase is quantitated by scintillation counting. Compounds are screened at 10 µM.

Table V. Secretion of IL-12 in Mouse Spleenic Macrophage

Compound 6 of this class inhibited IL-12 production in mouse splenic macrophages stimulated with LPS for 72 hrs. The compound shown in Table V strongly inhibited IL-12 production in these cells. A selective cyclooxygenase-2 (COX-2) inhibitor, rofecoxib was compared side by side in this experiment and no effect was observed with this compound.

Table-VI

SJL mice were immunized with keyhole limpet hemocyanin (KLH) in complete Freund's adjuvant (CFA). 12 days later regional lymph nodes were isolated and a proliferative response to KLH in the presence or absence of drug was performed (in presence of 3H thymidine). The results are expressed at Stimulation index (CPM+antigen/CPM no antigen). Similarly, mitogen induced concanavalin A (CON-A), IL-4, IL-2 induced T cell proliferation was measured in presence of compounds are shown in Table VI. A COX-2 inhibitor, rofecoxib was used in this experiment and it did not show any effect on T cells.

TABLE I

Inhibition of LPS induced TNF-α in THP-1 monocytic cells at 10 μM

| Compound No. | Inhibition (%) |
|---|---|
| 6 | 92 |
| 9 | 20 |
| Dexamethasone | 70 |

TABLE II

Inhibition of LPS induced cytokines in hPBMC at 10 μM

| | Inhibition (%) | | |
|---|---|---|---|
| Compound No. | IL-1β | IL-6 | TNF-α |
| 6 | 73 | 97 | 69.6* |
| 14 | ND | ND | 22.0 |
| 15 | ND | ND | 40.1 |
| 16 | ND | ND | 69.2 |
| 21 | ND | ND | 36.1 |
| 22 | ND | ND | 40.0 |
| Dexamethasone | 26 | 14 | 42.0* |

*Average of two experiments;
ND = Experiment not done

TABLE III

Effect of compounds in LPS induced Sepsis in mice (50 mg/kg body weight)

| | Inhibition (%) | |
|---|---|---|
| Compound No. | TNF-α | IL-6 |
| 6 | 50 | 30 |
| 9 | 45 | ND |
| Dexamethasone (5 mg/kg bw) | 70 | 50 |

TABLE IV

Effect of compound 6 on inhibition of TACE, MMP-1, MMP-9, PDE-3 and PDE-4 enzymes

| Compound | Inhibition at 10 μM (%) | | | | |
|---|---|---|---|---|---|
| No. | TACE | MMP-1 | MMP-9 | PDE-3 | PDE-4 |
| 6 | 15 | 12 | NE | 3 | 4 |

NE = No effect

TABLE V

IL-12, nitric oxide and TNF-α secretion following LPS stimulation of mouse spleenic macrophages at 10 μM concentration

| Compound | Mice Spleen Cells (% Inhibition) | | |
|---|---|---|---|
| No. | TNF-α | NO | IL-12 |
| 6 | 20 | 20 | 80 |

TABLE-VI

Inhibition of T cell proliferation at 10 μM concentration

| | Inhibition | | | | |
|---|---|---|---|---|---|
| Compound No. | CON A | Anti CD3 Abs | IL-2 | IL-4 | KLH Specific |
| 6 | +++ | ++++ | +++ | +++ | ++++ |

Inhibition:
+ = 0-20%,
++ = 21-60%,
+++ = 61-80%,
++++ = <80%;
all results at 10 μM drug concentration FIG. 1: Effect of Compounds in Collagen Induced Arthritis Model Arthritis induced in male DBA/1 Lac mice with bovine collagen (100 μg/mouse). Booster dose was given on Day 21 and started treatment when clinical score was about 2. Compounds 6, 9 and 22 (oral 50 mg/kg daily) significantly improved the arthritic scores in these animals. Dexamethasone was kept as positive control. Severity of each paw score was defined from 0=no erythma to 4=severe arthritis for the swollen paws with a maximum possible score of 16 for 4 paws (4×4) in one animal.

FIG. 2: Effect of Compounds in EAE Model of Mice

Multiple Sclerosis (MS) is an autoimmune disease and is regulated by cytokine levels. In order to test the effect of compound in multiple sclerosis (MS) model, experimental allergic encephalomyelitis (EAE) was induced in SJL/J mice. EAE is an autoimmune inflammatory disease of the central nervous system (CNS). The disease shows many similarities with the human MS, and hence is used as a model to test the potential efficacy of new drugs that may have applicability in MS. EAE was induced by injecting spinal chord homogenate where animals were treated with example compounds. The severity of EAE was established by clinical scores of paralysis. As shown in FIG. 2, the new compounds treated group showed complete prevention of EAE. These results indicate utility of the example compounds for the treatment of MS and other neurological disorders.

FIG. 3: Lowering of Inflammation in Carrageenan Induced Rats

Sprague-Dowley rats with average weight of 250 g (6-7 weeks of age) were randomized in three groups, and given 50 mg/kg oral dose of compound of example 6. Thirty minutes later carrageenan was administered in the sub-planter region of right hind paws. The control group received equal volume of water without any compound. Paw volume was measured after 2 and 3 hours. Dexamethasone at a concentration of 5 mg/kg was used as a positive control in this experiment. The compound has shown substantially lower the inflammation induced by carrageenan.

FIG. 4: Inhibition of IL-2 in Mouse Macrophage

Mouse peritoneal macrophages were cultured in 96 well plates at a density of $10^5$ cells/mL. They were pretreated with compound 22 for 30 min before they were independently challenged with LPS (1 μg/mL), Interferon Gamma (20 μg/mL or antiCD40 antibody (2 μg/mL). Incubation was continued for next 24 hrs and at the end IL-12 (p40) was measured by ELISA.

FIG. 5: Inhibition of CD40 Ligand-Mediated Synthesis of IL-12 (p40)

To further confirm the inhibition of IL-12 secretion mediated by CD40, induction of IL-12 (p40) was examined following activation of macrophages by soluble CD40 ligand, CD 154. Mouse peritoneal macrophages, were stimulated with 2 μg/mL of soluble CD 145 (Immunex) in the presence of compound 22. The compound showed prominent inhibition of IL-12.

FIG. 6: Inhibition of myelin basic protein (MBP) induced interferon-αSJL mice were immunized with 400 μg of myelin basic protein (MBP) in CFA on day 0 and 7 and regional lymph nodes were harvested on day 14 and cultured with MBP in the presence or absence of compound 22 for 72 h. Lymphocyte proliferation was determined by thymidine incorporation assay. Cell culture supernatants from MBP stimulated and compound 22 treated cells were assayed for gamma interferon using ELISA. Note the decrease in gamma interferon levels in spite of normal T cell proliferative response in compound 22 treated cell cultures.

FIG. 7: Reduction of Adjuvant Induced Arthritis in Rats

Male Lewis rats (~150 g) were immunized with *Mycobacterium butyricum* (1 mg) in incomplete Freund's adjuvant. Clinical symptoms of arthritis appeared between Day 12-14. The rats were randomized into the groups and treated daily with the vehicle or the drug. The clinical score of arthritis were monitored twice a week.

FIG. 8: Inhibition of TNF-α Levels in LPS-Induced Pyresis in Mice

SW mice were orally treated with dexamethasone (5 mg/kg body weight) and compound 22 dissolved in water at different doses. After 1 h of dosing LPS was administered (400 μg/kg, IP) and blood was collected after 90 min. TNF-α levels in sera were measured by ELISA.

FIG. 9: Effect of Compound 22 in Inflammatory Bowel Disease (IBD)

The Panel A shows the lowering of disease activity index (DAI) of intestinal bowel disease (IBD) induced by dextran sodium sulphate (DSS) in male SW mice. DAI is comprised of factors such as body weight, stool quality and occult blood content. A 4% solution of DSS was provided as drinking water and DAI was monitored twice a week for the induction of disease. Following this the animals were treated with a daily dose 50 mg/kg body weight of compound 22 in PEG400 formulations and the activity index was monitored twice a week.

The Panel B shows the improvement of body weight, a parameter for the amelioration of IBD, in 2,4,6-trinitrobenzene sulphonic acid (TNBS) induced IBD in rat. TNBS (30 mg) dissolved in 50% ethanol (0.25 mL) was rectally instilled into female rats (~250-300 g). The animals were dosed with the treatment compound at 100 mg/kg PO, for 15 days. The body weight change is represented as percentage of their initial day value.

The invention claimed is:

1. A compound of the formula (Ia)

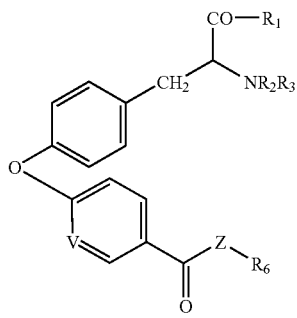

its derivatives, stereoisomers and its pharmaceutically acceptable salts wherein;

V is CH or N;

$R_1$ represents —$OR^{10}$; $NR^{11}R^{12}$;

$R_2$ and $R_3$ may be same or different and independently represent H, $COR^{13}$, substituted or unsubstituted groups selected from the group consisting of alkyl, alkenyl, aryl, heteroaryl, alkylsufonyl, alkylsulfinyl, arylsulfonyl, arylsulfinyl, alkylthio, arylthio and heterocyclyl; or $R_2$ and $R_3$ may together form a heterocyclic ring;

Z represents O, S or $NR^{14}$; when Z represents O or S, $R_6$ represents hydrogen or substituted or unsubstituted groups selected from the group consisting of alkyl, alkenyl, aryl, aralkyl, cycloalkyl, heteroaryl, heteroaralkyl and heterocyclyl; when Z represents $NR^{14}$, $R_6$ represents H, hydroxy, protected hydroxyl group, amino, substituted or unsubstituted groups selected from the group consisting of alkyl, haloalkyl, alkenyl, monoalkylamino, dialkylamino, aryl, aralkyl, cycloalkyl, heteroaryl, heteroaralkyl and heterocyclyl;

$R^{10}$ represents hydrogen, substituted or unsubstituted groups selected from the group consisting of alkyl, alkenyl, aryl, aralkyl, heteroaryl, and a counter ion;

$R^{11}$ and $R^{12}$ may be same or different and independently represent H, substituted or unsubstituted groups selected from the group consisting of alkyl, alkenyl and aryl or $R^{11}$ and $R^{12}$ together with nitrogen may represent substituted or unsubstituted mono or bicyclic saturated or unsaturated ring system which may contain one or more heteroatoms selected from O, S or N;

$R^{13}$ represents H, substituted or unsubstituted groups selected from the group consisting of alkyl, aryl, alkenyloxy, aryloxy, alkoxy and aralkoxy;

$R^{14}$ represents hydrogen or alkyl.

2. A compound according to claim 1 wherein $R_1$ is selected from the group consisting of amino, dialkylamino, isopropoxyl, hydroxyl, benzyloxyl, N-acetyl-perhydro-1,4-dithiaindinyl and perhydro-1,4-oxaza-indinyl.

3. A compound according to claim 1 wherein $R_2$ and $R_3$ are independently selected from the group consisting of hydrogen and p-toluenesulfonyl.

4. A compound according to claim 1 wherein $R_6$ is selected from the group consisting of hydroxyl, hydrogen and dialkylamino.

5. A compound according to claim 1 wherein Z is selected from NH or O.

6. A compound according to claim 1 selected from the group consisting of:

i) 2-amino-3-[4-(4-hydroxycarbamoylphenoxy)-phenyl]-propionic acid benzyl ester hydrochloric acid salt, ii) 2-amino-3-[4-(4-hydroxycarbamoylphenoxy)-phenyl]-propionic acid hydrochloric acid salt, iii) 4-[4-(2-amino-2-dimethylcarbamoylethyl)-phenoxy]-N-hydroxybenzamide hydrochloric acid salt, iv) 4-[4-(2-amino-2-isopropoxycarbonylethyl)-phenoxy]-benzoic acid, v) 2-amino-3-[4-(4-hydroxycarbamoylphenoxy)-phenyl]-propionic acid isopropyl ester, vi) 2-amino-3-[4-(4-hydroxycarbamoylphenoxy)-phenyl]-propionic acid sodium salt, vii) 2-amino-3-[4-(4-hydroxycarbamoylphenoxy)-phenyl]-propionic acid, viii) 2-amino-3-[4-(4-hydroxycarbamoylphenoxy)-phenyl]-propionic acid, and ix) 4-[4-(2-amino-2-carbamoylethyl)-phenoxy]-N-hydroxybenzamide.

7. A pharmaceutical composition comprising a compound of the formula (Ia) as defined in claim 3 and a pharmaceutically acceptable carrier, diluent, excipient or solvent.

8. A pharmaceutical composition according to claim 7 in the form of a tablet, capsule, powder, syrup, solution, aerosol or suspension.

9. A compound according to claim 1, wherein said pharmaceutically acceptable salt is selected from the hydrochloride, hydrobromide, potassium or magnesium salt.

10. A compound according to claim 6 selected from the group consisting of:

i) 2-amino-3-[4-(4-hydroxycarbamoylphenoxy)-phenyl]-propionic acid benzyl ester hydrochloric acid salt, ii) 2-amino-3-[4-(4-hydroxycarbamoylphenoxy)-phenyl]-propionic acid hydrochloric acid salt, iii) 4-[4-(2-amino-2-dimethylcarbamoylethyl)-phenoxy]-N-hydroxybenzamide hydrochloric acid salt, iv) 4-[4-(2-amino-2-isopropoxycarbonylethyl)-phenoxy]-benzoic acid, v) 2-amino-3-[4-(4-hydroxycarbamoylphenoxy)-phenyl]-propionic acid isopropyl ester, and vi) 2-amino-3-[4-(4-hydroxycarbamoylphenoxy)-phenyl]-propionic acid sodium salt.

11. The compound according to claim 10 2-amino-3-[4-(4-hydroxycarbamoylphenoxy)-phenyl]-propionic acid benzyl ester hydrochloric acid salt.

12. The compound according to claim 10 2-amino-3-[4-(4-hydroxycarbamoylphenoxy)-phenyl]-propionic acid hydrochloric acid salt.

13. The compound according to claim 10 4-[4-(2-amino-2-dimethylcarbamoylethyl)-phenoxy]-N-hydroxybenzamide hydrochloric acid salt.

14. The compound according to claim 10 4-[4-(2-amino-2-isopropoxycarbonylethyl)-phenoxy]-benzoic acid.

15. The compound according to claim 10 2-amino-3-[4-(4-hydroxycarbamoylphenoxy)-phenyl]-propionic acid isopropyl ester.

16. The compound according to claim 10 2-amino-3-[4-(4-hydroxycarbamoylphenoxy)-phenyl]-propionic acid sodium salt.

* * * * *

```
                       SEQUENCE LISTING

<160> NUMBER OF SEQ ID NOS: 4

<210> SEQ ID NO 1
<211> LENGTH: 7
<212> TYPE: PRT
<213> ORGANISM: Artificial Sequence
<220> FEATURE:
<223> OTHER INFORMATION: Coumarin-labelled peptide useful as a
      fluorogenic substrate for matrix metalloproteinases.
<220> FEATURE:
<221> NAME/KEY: MOD_RES
<222> LOCATION: 1
<223> OTHER INFORMATION: The first occurrence of Xaa is a modified or
      unusual amino acid Mca N-terminal modified
      proline.  "Mca" is N-terminal group
      (7-methoxycoumarin-4-yl) acetyl.
<220> FEATURE:
<221> NAME/KEY: MOD_RES
<222> LOCATION: 5
<223> OTHER INFORMATION: The second occurrence of Xaa is a modified or
      unusual amino acid Dpa.  "Dpa" is N3-
      [2,4-dinitrophenyl]-L-2,3-diaminopropionyl.
<220> FEATURE:
<221> NAME/KEY: VARIANT
<222> LOCATION: 1, 5
<223> OTHER INFORMATION: Xaa = Any Amino Acid
<300> PUBLICATION INFORMATION:
<301> AUTHORS: Knight, C.G., Willenbrock, F., Murphy, Gillian
<302> TITLE: A Novel Coumarin-labelled Peptide for Sensitive Co
<303> JOURNAL: Fed. European Biochemical Societies
<304> VOLUME: 296
<305> ISSUE: 3
<306> PAGES: 263-266
<307> DATE: 1992-01-01

<400> SEQUENCE: 1

Xaa Leu Gly Leu Xaa Ala Arg
 1               5

<210> SEQ ID NO 2
<211> LENGTH: 3
<212> TYPE: PRT
<213> ORGANISM: Artificial Sequence
```

```
<220> FEATURE:
<223> OTHER INFORMATION: Coumarin-labelled peptide useful as a
      fluorogenic substrate for matrix metalloproteinases.
<220> FEATURE:
<221> NAME/KEY: MOD_RES
<222> LOCATION: 1
<223> OTHER INFORMATION: The occurrence of Xaa is a modified or unusual
      amino acid Mca N-terminal modified proline.  "Mca"
      is N-terminal group (7-methoxycoumarin-4-yl)
      acetyl.
<220> FEATURE:
<221> NAME/KEY: VARIANT
<222> LOCATION: 1
<223> OTHER INFORMATION: Xaa = Any Amino Acid
<300> PUBLICATION INFORMATION:
<301> AUTHORS: Knight, C.G., Willenbrock, F., Murphy, Gillian
<302> TITLE: A Novel Coumarin-labelled Peptide for Sensitive Co
<303> JOURNAL: Fed. European Biochemical Societies
<304> VOLUME: 296
<305> ISSUE: 3
<306> PAGES: 263-266
<307> DATE: 1992-01-01

<400> SEQUENCE: 2

Xaa Leu Gly
 1

<210> SEQ ID NO 3
<211> LENGTH: 12
<212> TYPE: PRT
<213> ORGANISM: Artificial Sequence
<220> FEATURE:
<223> OTHER INFORMATION: Coumarin-labelled peptide useful as a
      fluorogenic substrate for matrix metalloproteinases.
<220> FEATURE:
<221> NAME/KEY: MOD_RES
<222> LOCATION: 1
<223> OTHER INFORMATION: The first occurrence of Xaa is a modified or
      unusual amino acid Mca N-terminal modified
      praline.  "Mca" is N-terminal group
      (7-methoxycoumarin-4-yl) acetyl.
<220> FEATURE:
<221> NAME/KEY: MOD_RES
<222> LOCATION: 7
<223> OTHER INFORMATION: The second occurrence of Xaa is a modified or
      unusual amino acid Dpa.  "Dpa is N3-
      [2,4-dinitrophenyl]-L-2,3-diaminopropionyl.
<220> FEATURE:
<221> NAME/KEY: VARIANT
<222> LOCATION: 1, 7
<223> OTHER INFORMATION: Xaa = Any Amino Acid

<400> SEQUENCE: 3

Xaa Leu Ala Gln Ala Val Xaa Arg Ser Ser Ser Arg
 1               5                  10

<210> SEQ ID NO 4
<211> LENGTH: 5
<212> TYPE: PRT
<213> ORGANISM: Artificial Sequence
<220> FEATURE:
<223> OTHER INFORMATION: Coumarin-labelled peptide useful as a
      fluorogenic substrate for matrix metalloproteinases.
<220> FEATURE:
<221> NAME/KEY: MOD_RES
<222> LOCATION: 1
<223> OTHER INFORMATION: The occurrence of Xaa is a modified or unusual
      amino acid Mca N-terminal modified proline.  "Mca"
      is N-terminal group (7-methoxycoumarin-4-yl)
      acetyl.
<220> FEATURE:
<221> NAME/KEY: VARIANT
<222> LOCATION: 1
<223> OTHER INFORMATION: Xaa = Any Amino Acid
```

```
<400> SEQUENCE: 4

Xaa Leu Ala Gln Ala
 1               5
```